(12) United States Patent
Decker

(10) Patent No.: US 6,825,013 B2
(45) Date of Patent: Nov. 30, 2004

(54) **ISOLATION OF BIOSYNTHESIS GENES FOR PSEUDO-OLIGOSACCHARIDES FROM *STREPTOMYCES GLAUCESCENS* GLA.O, AND THEIR USE**

(75) Inventor: Heinrich Decker, Bremtal (DE)

(73) Assignee: Avantis Pharma Deutschland GmbH, Frankfurt (DE)

( * ) Notice: Subject to any disclaimer, the term of this patent is extended or adjusted under 35 U.S.C. 154(b) by 148 days.

(21) Appl. No.: 09/922,683

(22) Filed: Aug. 7, 2001

(65) Prior Publication Data

US 2002/0192793 A1 Dec. 19, 2002

Related U.S. Application Data

(62) Division of application No. 09/194,905, filed as application No. PCT/EP97/02826 on May 30, 1997, now Pat. No. 6,306,627.

(30) Foreign Application Priority Data

Jun. 7, 1996 (DE) .......................................... 196 22 783
May 30, 1997 (WO) .......................................... 97/02826

(51) Int. Cl.⁷ ........................... C12P 9/12; C12P 21/06; C12N 9/00; C12N 1/20; C12N 1/12
(52) U.S. Cl. ............................... 435/100; 435/4; 435/6; 435/69.1; 435/41; 435/94; 435/95; 435/96; 435/97; 435/98; 435/99; 435/252.3; 435/252.31; 435/252.33; 435/253.5; 435/254.1; 435/254.11; 435/254.5; 435/254.21; 435/320.1; 536/23.2; 536/23.4; 536/23.7; 530/350
(58) Field of Search .................. 435/4, 6–29, 183–220, 435/223, 41, 94–101, 252.3, 252.31, 252.33, 253.5, 254.1, 254.11, 254.5, 254.21, 320.1, 69.1, 71.2, 71.3, 72, 85, 120, 109; 536/23.2, 23.7, 23.4, 23.74

(56) References Cited

U.S. PATENT DOCUMENTS 5,753,501 A    5/1998 Crueger et al.

FOREIGN PATENT DOCUMENTS

DE        22 09 834 A1      9/1973
DE        EP 0 730 029 A2   9/1996

OTHER PUBLICATIONS

Stockmann, M. & Piepersberg, W., "Gene Probes for the Detection of 6–Deoxyhexose Metabolism in Secondary Meabolite–Producing Streptmoycetes," FEMS Microbiology Letters, vol. 90, No. 2, (Jan. 1, 1992), pp. 185–190.

Primary Examiner—Manjunath Rao
(74) Attorney, Agent, or Firm—Karen I. Krapen

(57) ABSTRACT

The invention relates to a recombinant DNA molecule which comprises genes for biosynthesizing acarbose and homologous pseudo-oligosaccharides; to oligonucleotide primers for the PCR amplification of the molecule; to proteins which can be obtained by expressing the genes located on a molecule; to vectors and host cells which comprise the above-mentioned DNA molecule; to proteins which are encoded by the DNA molecule; to proteins which are expressed by means of said vectors in said host cells; to processes for preparing acarbose by introducing the characterized genes into appropriate host organisms and/or eliminating these genes from the host organisms; to processes for completing the gene cluster of genes for biosynthesizing acarbose, to processes for isolating analogous gene clusters in organisms other than *Streptomyces glaucescens* GLA.O, to processes for mutating promoters of endogenous acarbose biosynthesis genes for the purpose of increasing the yield of acarbose, to the use of *Streptomyces glaucescens* GLA.O for preparing acarbose and for preparing mutants of *Streptomyces glaucescens* GLA.O which are optimized with regard to the acarbose yield.

2 Claims, 5 Drawing Sheets

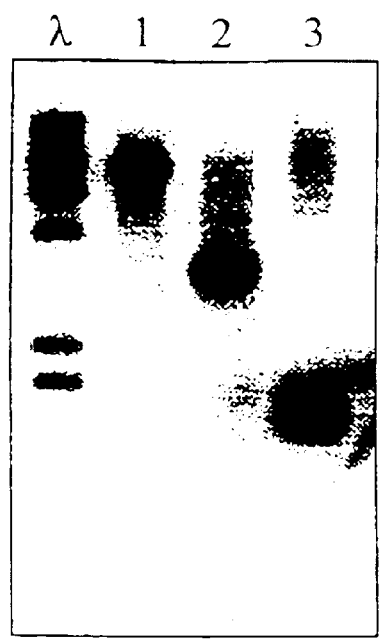
Fig. 1: Southern hybridization using *Streptomyces glaucescens* GLA.O

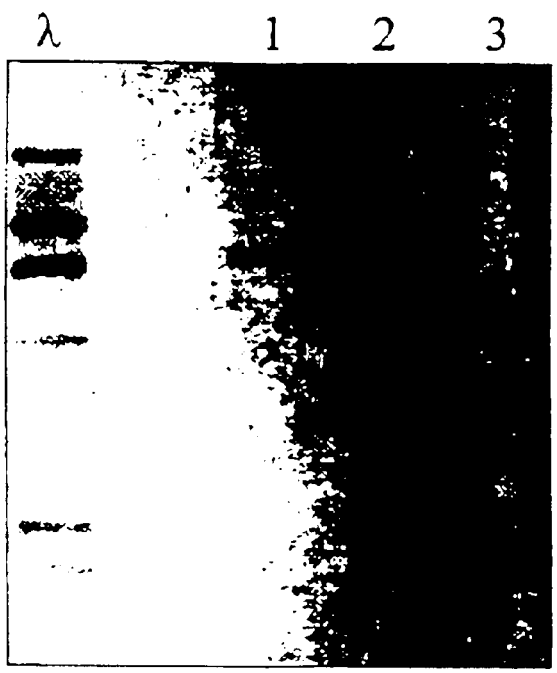
FIG. 2: Southern hybridization using *Streptomyces glaucescens* GLA.O

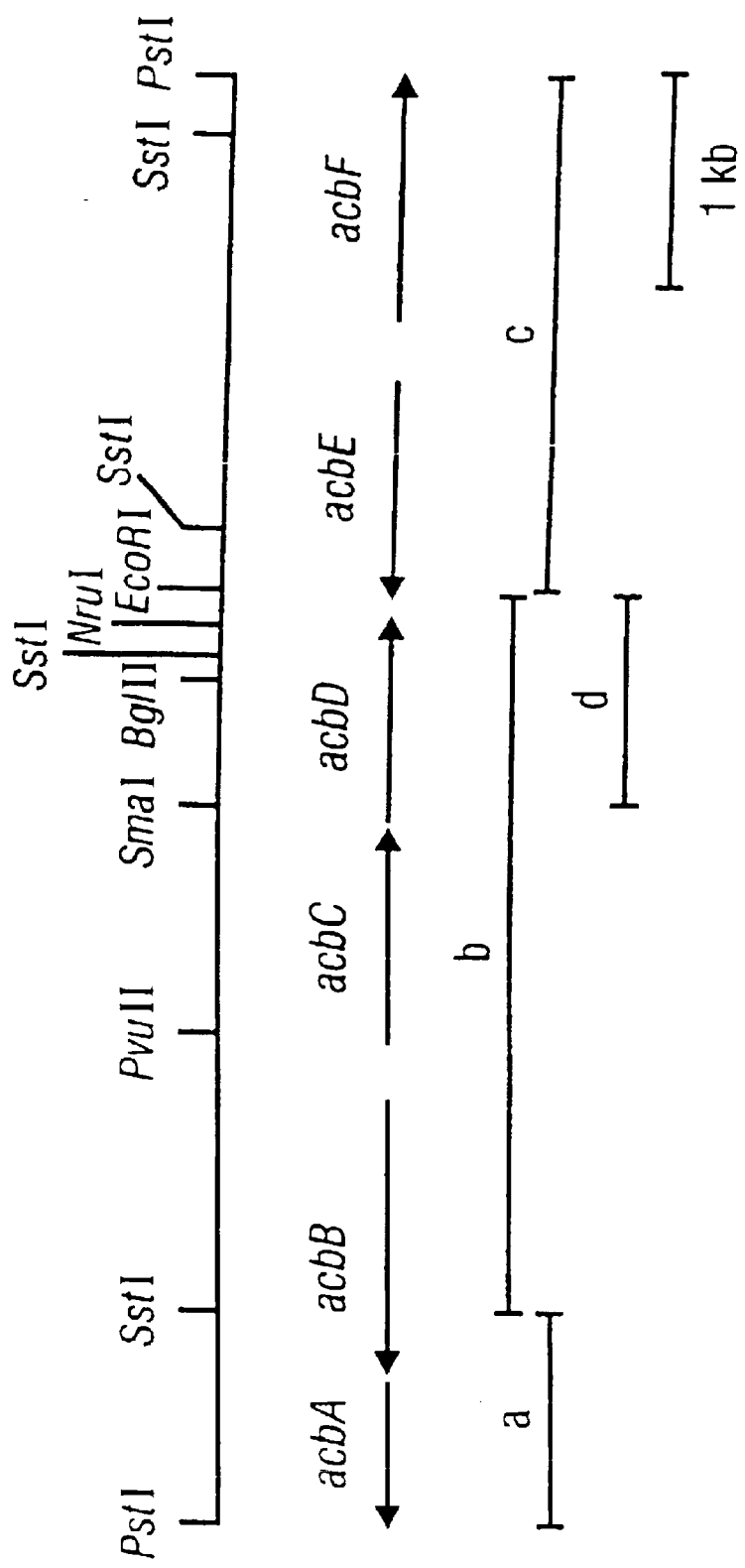
Fig. 3: Restriction map of the 6.8 kb PstI fragment from *Streptomyces glaucescens* GLA.O

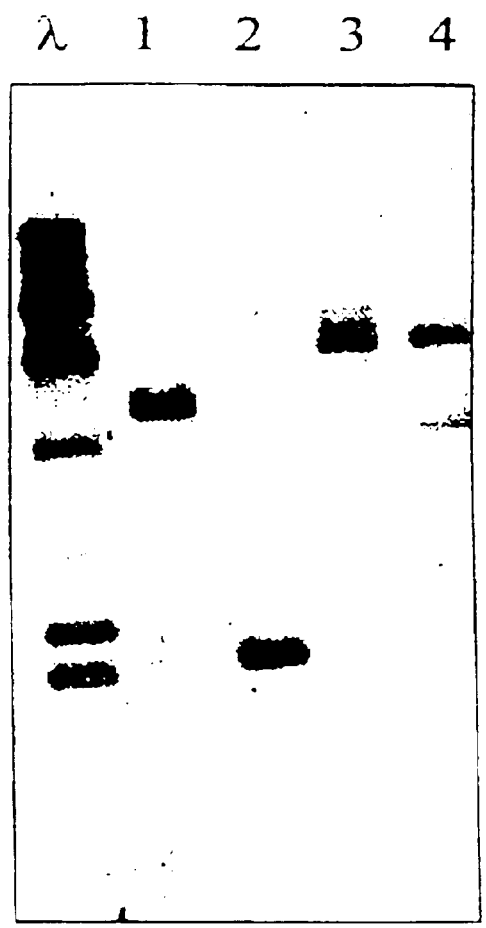
Fig. 4: Southern hybridization using *Streptomyces glaucescens* Δacb

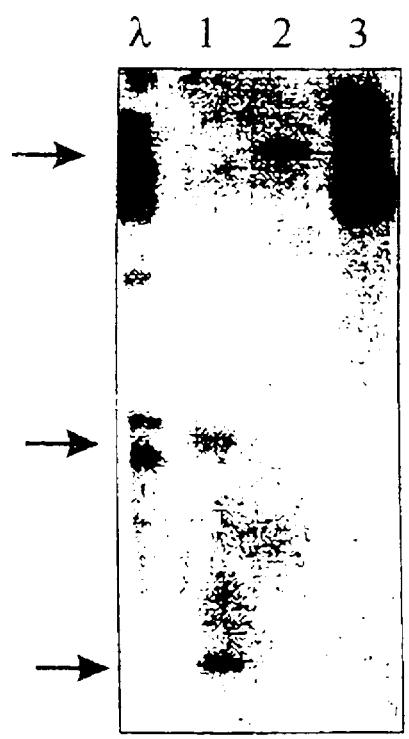
Fig. 5: Southern hybridization using *Actinoplanes* sp. SE50/100

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer"

(xi) SEQUENCE DESCRIPTION: SEQ ID NO: 1:

CSGGSGSSGC SGGSTTCATS GG                                  22

(2) INFORMATION FOR SEQ ID NO: 2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer"

(xi) SEQUENCE DESCRIPTION: SEQ ID NO: 2:

GGGWVCTGGY VSGGSCCGTA GTTG                              24

(2) INFORMATION FOR SEQ ID NO: 3:

(i) SEQUENCE CHARACTERISTICS:
      (A) LENGTH: 546 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 3:

CCCGGGCGGG GCGGGGTTCA TCGGCTCCGC CTACGTCCGC CGGCTCCTGT CGCCCGGGGC    60

CCCCGGCGGC GTCGCGGTGA CCGTCCTCGA CAAACTCACC TACGCCGGCA GCCTCGCCCG   120

```
CCTGCACGCG GTGCGTGACC ATCCCGGCCT CACCTTCGTC CAGGGCGACG TGTGCGACAC      180

CGCGCTCGTC GACACGCTGG CCGCGCGGCA CGACGACATC GTGCACTTCG CGGCCGAGTC      240

GCACGTCGAC CGCTCCATCA CCGACAGCGG TGCCTTCACC CGCACCAACG TGCTGGGCAC      300

CCAGGTCCTG CTCGACGCCG CGCTCCGCCA CGGTGTGCGC ACCCTCGTGC ACGTCTCCAC      360

CGACGAGGTG TACGGCTCCC TCCCGCACGG GGCCGCCGCG GAGAGCGACC CCCTGCTCCC      420

GACCTCGCCG TACGCGGCGT CGAAGGCGGC CTCGGACCTC ATGGCGCTCG CCCACCACCG      480

CACCCACGGC CTGGACGTCC GGGTGACCCG CTGTTCGAAC AACTACGGCC CGCACCAGTT      540

CCCGGG                                                                 546

(2) INFORMATION FOR SEQ ID NO: 4:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CCCCGGGTGC TGGTAGGGGC CGTAGTTGTT GGAGCAGCGG GTGATGCGCA CGTCCAGGCC       60

GTGGCTGACG TGCATGGCCA GCGCGAGCAG GTCGCCCGAC GCCTTGGAGG TGGCATAGGG      120

GCTGTTGGGG CGCAGCGGCT CGTCCTCCGT CCACGACCCC GTCTCCAGCG AGCCGTAGAC      180

CTCGTCGGTG GACACCTGCA CGAAGGGGGC CACGCCGTGC CGCAGGGCCG CGTCGAGGAG      240

TGTCTGCGTG CCGCCGGCGT TGGTCCGCAC GAACGCGGCG GCATCGAGCA GCGAGCGGTC      300

CACGTGCGAC TCGGCGGCGA GGTGCACGAC CTGGTCCTGG CCGGCCATGA CCCGGTCGAC      360

CAGGTCCGCG TCGCAGATGT CGCCGTGGAC GAAGCGCAGC CGGGGGTGGT CGCGGACCGG      420

GTCGAGGTTG GCGAGGTTGC CGGCGTAGCT CAGGGCGTCG AGCACGGTGA CGACGGCGTC      480

GGGCGGCCCG TCCGGACCGA GGAGGGTGCG GACGTAGTGC GAGCCCATGA ACCCCGCCGC      540

C                                                                      541

(2) INFORMATION FOR SEQ ID NO: 5:

(i) SEQUENCE CHARACTERISTICS:
        (A) LENGTH: 180 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 5:

Ala Ala Gly Phe Met Gly Ser His Tyr Val Arg Thr Leu Leu Gly Pro
1               5                   10                  15

Asp Gly Pro Pro Asp Ala Val Val Thr Val Leu Asp Ala Leu Ser Tyr
            20                  25                  30

Ala Gly Asn Leu Ala Asn Leu Asp Pro Val Arg Asp His Pro Arg Leu
        35                  40                  45

Arg Phe Val His Gly Asp Ile Cys Asp Ala Asp Leu Val Asp Arg Val
    50                  55                  60

Met Ala Gly Gln Asp Gln Val Val His Leu Ala Ala Glu Ser His Val
65                  70                  75                  80

Asp Arg Ser Leu Leu Asp Ala Ala Ala Phe Val Arg Thr Asn Ala Gly
                85                  90                  95
```

```
Gly Thr Gln Thr Leu Leu Asp Ala Ala Leu Arg His Gly Val Ala Pro
            100                 105                 110

Phe Val Gln Val Ser Thr Asp Glu Val Tyr Gly Ser Leu Glu Thr Gly
            115                 120                 125

Ser Trp Thr Glu Asp Glu Pro Leu Arg Pro Asn Ser Pro Tyr Ala Thr
            130                 135             140

Ser Lys Ala Ser Gly Asp Leu Leu Ala Leu Ala Met His Val Ser His
145                 150                 155                 160

Gly Leu Asp Val Arg Ile Thr Arg Cys Ser Asn Asn Tyr Gly Pro Tyr
                165                 170                 175

Gln His Pro Gly
            180

(2) INFORMATION FOR SEQ ID NO: 6:

(i) SEQUENCE CHARACTERISTICS:
        (A) LENGTH: 181 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 6:

Pro Gly Gly Ala Gly Phe Ile Gly Ser Ala Tyr Val Arg Arg Leu Leu
1               5                   10                  15

Ser Pro Gly Ala Pro Gly Gly Val Ala Val Thr Val Leu Asp Lys Leu
            20                  25                  30

Thr Tyr Ala Gly Ser Leu Ala Arg Leu His Ala Val Arg Asp His Pro
            35                  40                  45

Gly Leu Thr Phe Val Gln Gly Asp Val Cys Asp Thr Ala Leu Val Asp
        50                  55                  60

Thr Leu Ala Ala Arg His Asp Asp Ile Val His Phe Ala Ala Glu Ser
65                  70                  75                  80

His Val Asp Arg Ser Ile Thr Asp Ser Gly Ala Phe Thr Arg Thr Asn
                85                  90                  95

Val Leu Gly Thr Gln Val Leu Leu Asp Ala Ala Leu Arg His Gly Val
            100                 105                 110

Arg Thr Leu Val His Val Ser Thr Asp Glu Val Tyr Gly Ser Leu Pro
            115                 120                 125

His Gly Ala Ala Ala Glu Ser Asp Pro Leu Leu Pro Thr Ser Pro Tyr
            130                 135             140

Ala Ala Ser Lys Ala Ala Ser Asp Leu Met Ala Leu Ala His His Arg
145                 150                 155                 160

Thr His Gly Leu Asp Val Arg Val Thr Arg Cys Ser Asn Asn Tyr Gly
                165                 170                 175

Pro His Gln Phe Pro
            180

(2) INFORMATION FOR SEQ ID NO: 7:

(i) SEQUENCE CHARACTERISTICS:
        (A) LENGTH: 6854 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 7:

```
CTGCAGGGTT CCCTGGTGCA CGACCCGCCC CTGGTCGACG ACCAGGGCGC TGTCGCAGAT      60

CGCGGCGATG TCGGCGATGT CGTGGCTGGT GAGCACCACG GTGGTGCCCA GTTCCCGGTG     120

GGCGCGGTTG ACCAGCCGGC GCACCGCGTC CTTCAGCACC ATGTCGAGGC CGATCGTGGG     180

CTCGTCCCAG AACAGCACGG CCGGGTCGTG CAGCAGGCTC GCCGCGATCT CGGCGCGCAT     240

GCGCTGTCCG AGGCTGAGCT GCCGCACGGG GGTGGACCCC AGCGCGTCGA TGTCGAGGAG     300

GTCCCGGAAC AGGGCGAGGT TGCGCCGGTA GACCGGTCCG GGGATGTCGT AGATGCGGCG     360

CAGGATGCGG AAGGAGTCGG GTACCGACAG GTCCCACCAG AGCTGGCTGC GCTGGCCGAA     420

GACGACGCCG ATCGTGCGGG CGTTGCGCTG CCGGTGCCGG TAGGGCTCCA GCCCGGCGAC     480

CGTGCAGCGG CCGGAGGTGG GGGTCATGAT GCCGGTCAGC ATCTTGATCG TGGTCGACTT     540

GCCGGCTCCG TTGGCGCCGA TGTAGGCGGT CTTCGTGCCG GCCGGTATCT CGAAGGAGAC     600

GTCGTCGACG GCGCGCACGA CGCGGTACCG GCGGGTCAGG AGGGTGGAGA GGCTGCCGAG     660

CAGGCCGGGC TCGCGTTCGG CCAGCCGGAA CTCCTTGACG AGGTGTTCGG CCACGATCAC     720

GCGATCACCC GCTCGACGGC CGTCTCCAGC AGGCGCAGGC CCTCGTCGAG CAGCGCCTCG     780

TCGAGGGTGA CGGCGGTGC CAGCCGCAGG ATGTGGCCGC CCAGGGAGGT GCGCAGCCCC     840

AGGTCGAGGG CGGTGGTGTA GACGGCCCGG GCGGTCTCGG GGGCGGGTGC CCGGCCGACG     900

GCGTCGGTGA CGAACTCCAG GCCCCACAGC AGTCCGAGGC CGCGTACCTG GCCGAGCTGG     960

GGGAAGCGGG ACTCCAGGGC GCGCAGCCGC TCCTGGATGA GCTCGCCGAG GACGCGCACG    1020

CGGTCGATCA GCCGGTCGCG CTCGACGACC TCCAGCGTGG CGCGGGCGGC GGCGATCCCC    1080

AGTGGGTTGC TCGCGTACGT CGAGGCGTAC GCCCCGGGGT GGCCGCCTCC GGCCTGCGCA    1140

GCTTCCGCGC GTCCGGCCAG CACGGCGAAG GGGAATCCGC TCGCGGTGCC CTTGGACAGC    1200

ATCGCCAGGT CCGGCTCGAT GCCGAACAGT TCGCTGGCGA GGAAGGCGCC GGTGCGCCCG    1260

CCGCCGGTGA GGACCTCGTC GGCGACGAGC AGCACGCCGC CGTCCCGGCA GGCGCCGGCG    1320

ATCCGCTCCC AGTAGCCGGG GGGCGGCACG ATGACGCCTG CCGCGCCGAG GACGGGTTCG    1380

AAGACCAGGG CCGAGACGTT GGGCTTCTCC GCGATGTGCC GGCGCACGAG GGTCGCGCAC    1440

CGCACGTCGC ACGAGGGGTA CTCCAGGCCC AGGGGACAGC GGTAGCCAGT AGGGGCTGTA    1500

GCCAGCACGC TGTTGCCGCT GAAGGCCTGG TGGCCGATGT CCCAGTGGAC CAGCATCCGG    1560

GCGCCCATGG TCTTGCCGTG GAAGCCGTGG CGCAGGGCGC AGATCCGGTT GCGGCCCGGC    1620

GCGGCGGTCG CCTGGACGAC CCGCAGGGCG GCCTCGACCA CCTCCGCGCC GGTGGAGAAG    1680

AAGGCGTAGG TGTCGAGCTG TTCGGGCAGC AGCCTGGCGA GCAGTTCCAG CAGGCCGGCG    1740

CGGTCCGGCG TGGCGCTGTC GTGGACGTTC CACAGGCGGC GGGCCTGGGT GGTGAGTGCC    1800

TCGACGACCT CCGGGTGCCC GTGGCCCAGT GACTGGGTGA GGGTCCCGGC CGCGAAGTCG    1860

AGGTACTGGT TGCCGTCCAG GTCGGTCAGA ACGGACCGC GTCCCTCGGC GAAGACCCGG    1920

CGTCCGTGGA CGGCTTCCTC GGAGGCGCCC GGCGCCAGGT GGCGGGCCTC CCGTGCCAGG    1980

TGCTGTGTCT GCCGTAAGCC TGTCATCGCT GCCTCTGCTC GTCGGACCGG CTGACGCGAT    2040

CGCCGGCGAA CTGCGTTGTG GCGCACCACG GTTGGGCGG CTCGGCGCTG AGTCAAACAC    2100

TTGAACACAC ACCGCTGCAA GAGTTTGCGG GTTGTTTCAG AAAGTTGTTG CGAGCGGCCC    2160

CGGCACTCTG GTTGAGTCGA CGTGCTTACG GCGCCACCAC GCCTCACGTT CGAGGAGGGA    2220

CCTGTGAGAA CAAGCCCGCA GACCGACCCG CTCCCGCGGA GGCCGAGGTG AAGGCCCTGG    2280

TCCTGGCAGG TGGAACCGGC AGCAGACTGA GGCCGTTCAC CCACACCGCC GCCAAGCAGC    2340
```

-continued

```
TGCTCCCCAT CGCCAACAAG CCCGTGCTCT TCTACGCGCT GGAGTCCCTC GCCGCGGCGG    2400

GTGTCCGGGA GGCCGGCGTC GTCGTGGGCG CGTACGGCCG GGAGATCCGC GAACTCACCG    2460

GCGACGGCAC CGCGTTCGGG TTACGCATCA CCTACCTCCA CCAGCCCCGC CCGCTCGGTC    2520

TCGCGCACGC GGTGCGCATC GCCCGCGGCT TCCTGGGCGA CGACGACTTC CTGCTGTACC    2580

TGGGGGACAA CTACCTGCCC CAGGGCGTCA CCGACTTCGC CCGCCAATCG GCCGCCGATC    2640

CCGCGGCGGC CCGGCTGCTG CTCACCCCGG TCGCGGACCC GTCCGCCTTC GGCGTCGCGG    2700

AGGTCGACGC GGACGGGAAC GTGCTGCGCT TGGAGGAGAA ACCCGACGTC CCGCGCAGCT    2760

CGCTCGCGCT CATCGGCGTG TACGCCTTCA GCCCGGCCGT CCACGAGGCG GTACGGGCCA    2820

TCACCCCCTC CGCCCGCGGC GAGCTGGAGA TCACCCACGC CGTGCAGTGG ATGATCGACC    2880

GGGGCCTGCG CGTACGGGCC GAGACCACCA CCCGGCCCTG GCGCGACACC GGCAGCGCGG    2940

AGGACATGCT GGAGGTCAAC CGTCACGTCC TGGACGGACT GGAGGGCCGC ATCGAGGGGA    3000

AGGTCGACGC GCACAGCACG CTGGTCGGCC GGGTCCGGGT GGCCGAAGGC GCGATCGTGC    3060

GGGGGTCACA CGTGGTGGGC CCGGTGGTGA TCGGCGCGGG TGCCGTCGTC AGCAACTCCA    3120

GTGTCGGCCC GTACACCTCC ATCGGGGAGG ACTGCCGGGT CGAGGACAGC GCCATCGAGT    3180

ACTCCGTCCT GCTGCGCGGC GCCCAGGTCG AGGGGGCGTC CCGCATCGAG GCGTCCCTCA    3240

TCGGCCGCGG CGCCGTCGTC GGCCCGGCCC CCCGTCTCCC GCAGGCTCAC CGACTGGTGA    3300

TCGGCGACCA CAGCAAGGTG TATCTCACCC CATGACCACG ACCATCCTCG TCACCGGCGG    3360

AGCGGGCTTC ATTCGCTCCG CCTACGTCCG CCGGCTCCTG TCGCCCGGGG CCCCCGGCGG    3420

CGTCGCGGTG ACCGTCCTCG ACAAACTCAC CTACGCCGGC AGCCTCGCCC GCCTGCACGC    3480

GGTGCGTGAC CATCCCGGCC TCACCTTCGT CCAGGGCGAC GTGTGCGACA CCGCGCTCGT    3540

CGACACGCTG GCCGCGCGGC ACGACGACAT CGTGCACTTC GCGGCCGAGT CGCACGTCGA    3600

CCGCTCCATC ACCGACAGCG GTGCCTTCAC CCGCACCAAC GTGCTGGGCA CCCAGGTCCT    3660

GCTCGACGCC GCGCTCCGCC ACGGTGTGCG CACCTTCGTG CACGTCTCCA CCGACGAGGT    3720

GTACGGCTCC CTCCCGCACG GGGCCGCCGC GGAGAGCGAC CCCCTGCTTC CGACCTCGCC    3780

GTACGCGGCG TCGAAGGCGG CCTCGGACCT CATGGCGCTC GCCCACCACC GCACCCACGG    3840

CCTGGACGTC CGGGTGACCC GCTGTTCGAA CAACTTCGGC CCCCACCAGC ATCCCGAGAA    3900

GCTCATACCG CGCTTCCTGA CCAGCCTCCT GTCCGGCGGC ACCGTTCCCC TCTACGGCGA    3960

CGGGCGGCAC GTGCGCGACT GGCTGCACGT CGACGACCAC GTCAGGGCCG TCGAACTCGT    4020

CCGCGTGTCG GGCCGGCCGG GAGAGATCTA CAACATCGGG GGCGGCACCT CGCTGCCCAA    4080

CCTGGAGCTC ACGCACCGGT TGCTCGCACT GTGCGGCGCG GGCCCGGAGC GCATCGTCCA    4140

CGTCGAGAAC CGCAAGGGGC ACGACCGGCG CTACGCGGTC GACCACAGCA AGATCACCGC    4200

GGAACTCGGT TACCGGCCGC GCACCGACTT CGCGACCGCG CTGGCCGACA CCGCGAAGTG    4260

GTACGAGCGG CACGAGGACT GGTGGCGTCC CCTGCTCGCC GCGACATGAC GTCGGGCCGG    4320

ACCGCAACCA CCGGCCCCGG CCGGCACACC GCCGCCCGCG GCCGGTGGCC GGCCGGTCAG    4380

CGTCCGTGAG CCGGGCGCCG GCCGCCCCGC GGGCCGGCGG CGGTGGACCC CCGGACCACC    4440

AGTTCCGGCA TGAAGACGAA TTCGGTGCGC GGCGGCGGCG TTCCGCTCAT CTCCTCCAGC    4500

AGTGCGTCCA CGGCGACCTG CCCCATCGCC TTGACGGGCT GTCTGATGGT GGTCAGGGGA    4560

GGGTCGGTGA AGGCCATGAG CGGCGAGTCG TCGAAGCCGA CCACCGAGAT GTCACCGGGA    4620

ACCGTGAGAC CCCGCCGGCG CGCGGCCCGC ACGGCGCCGA GGGCCATCAT GTCGCTGGCG    4680
```

| | |
|---|---|
| CACATGACGG CGGTGCAGCC CAGGTCGATC AGCGCGGACG CGGCGGCCTG GCCCCCTCC | 4740 |
| AGGGAGAACA GCGAGTGCTG CACGAGCTCC TCGGACTCCC GCGCCGACAC TCCCAGGTGC | 4800 |
| TCCCGCACGC CGGCCCGGAA CCCCTCGATC TTCCGCTGCA CCGGCACGAA GCGGGCGGGC | 4860 |
| CCGACGGCGA GGCCGACGCG CTCGTGCCCC AGCTCCGCCA GGTGCGCCAC GGCCAGGCGC | 4920 |
| ATCGCGGCCC GGTCGTCCGG GGAGACGAAG GGTGCCTCGA TCCGGGGCGA GAACCCGTTC | 4980 |
| ACGAGGACGA AGGGCACCTG CCGCTCGTGC AGCCGGCCGT ACCGTCCGGT CTCGGCGGTG | 5040 |
| GTGTCCGCGT GCAGTCCGGA GACGAAGATG ATGCCGGACA CCCCGCGGTC CACGAGCATC | 5100 |
| TCCGTGAGTT CGTCCTCGGT CGAGCCGCCC GGGGTCTGCG TGGCGAGCAC GGGCGTGTAG | 5160 |
| CCCTGACGCG TGAGCGCCTG CCCCATCACC TGGGCCAGTG CGGGGAAGAA GGGGTTGTCC | 5220 |
| AGTTCGGGGG TGACCAGTCC GACCAGCTCG GCGCGGCGCT GTCGCGCCGG CTGCTCGTAG | 5280 |
| CCCAGCGCGT CCAGTGCGGT CAGCACCGAG TCGCGGGTGC CGGTGGCCAC ACCGCGCGCA | 5340 |
| CCGTTCAGCA CCCGGCTGAC CGTGGCCTTG CTGACGCCCG CCCGGGCTGC GATGTCGGCG | 5400 |
| AGCCGCATGG TCATGGCAAC GCACTCTACC TGTCGGGGCG TCAGGGCGTG CCCACCGCGC | 5460 |
| GCGGAACCGG CGGACTGCGG GGCACGGCCC GTCCGCCGCC CACGGACCAC GCGCCCGAAA | 5520 |
| CGATGGCTGA AAATGCTTGC AGCAAATTGC CGCAACGTCT TTCGGCGGCT TTTCGATCCT | 5580 |
| GTTACGTTCC TGGCAACCCC GGCGCCGCGC AGAAGCGGTT GGCGTGAGGC GTCCAGACCT | 5640 |
| CCGCCCGATT CCGGGATCAC TCAGGGGAGT TCACAATGCG GCGTGGCATT GCGGCCACCG | 5700 |
| CGCTGTTCGC GGCTGTGGCC ATGACGGCAT CGGCGTGTGG CGGGGGCGAC AACGGCGGAA | 5760 |
| GCGGTACCGA CGCGGGCGGC ACGGAGCTGT CGGGGACCGT CACCTTCTGG GACACGTCCA | 5820 |
| ACGAAGCCGA GAAGGCGACG TACCAGGCCC TCGCGGAGGG CTTCGAGAAG GAGCACCCGA | 5880 |
| AGGTCGACGT CAAGTACGTC AACGTCCCGT TCGGCGAGGC GAACGCCAAG TTCAAGAACG | 5940 |
| CCGCGGGCGG CAACTCCGGT GCCCCGGACG TGATGCGTAC GGAGGTCGCC TGGGTCGCGG | 6000 |
| ACTTCGCCAG CATCGGCTAC CTCGCCCCGC TCGACGGCAC GCCCGCCCTC GACGACGGGT | 6060 |
| CGGACCACCT TCCCCAGGGC GGCAGCACCA GGTACGAGGG GAAGACCTAC GCGGTCCCGC | 6120 |
| AGGTGATCGA CACCCTGGCG CTCTTCTACA ACAAGGAACT GCTGACGAAG GCCGGTGTCG | 6180 |
| AGGTGCCGGG CTCCCTCGCC GAGCTGAAGA CGGCCGCCGC CGAGATCACC GAGAAGACCG | 6240 |
| GCGCGAGCGG CCTCTACTGC GGGGCGACGA CCCGTACTTG GTTCCTGCCC TACCTCTACG | 6300 |
| GGGAGGGCGG CGACCTGGTC GACGAGAAGA ACAAGACCGT CACGGTCGAC GACGAAGCCG | 6360 |
| GTGTGCGCGC CTACCGCGTC ATCAAGGACC TCGTGGACAG CAAGGCGGCC ATCACCGACG | 6420 |
| CGTCCGACGG CTGGAACAAC ATGCAGAACG CCTTCAAGTC GGGCAAGGTC GCCATGATGG | 6480 |
| TCAACGGCCC CTGGGCCATC GAGGACGTCA AGGCGGGAGC CCGCTTCAAG GACGCCGGCA | 6540 |
| ACCTGGGGGT CGCCCCCGTC CCGGCCGGCA GTGCCGGACA GGGCTCTCCC CAGGGCGGGT | 6600 |
| GGAACCTCTC GGTGTACGCG GGCTCGAAGA ACCTCGACGC CTCCTACGCC TTCGTGAAGT | 6660 |
| ACATGAGCTC CGCCAAGGTG CAGCAGCAGA CCACCGAGAA GCTGAGCCTG CTGCCCACCC | 6720 |
| GCACGTCCGT CTACGAGGTC CCGTCCGTCG CGGACAACGA GATGGTGAAG TTCTTCAAGC | 6780 |
| CGGCCGTCGA CAAGGCCGTC AACGGCCGT GGATCGCCGA GGGCAATGCC CTCTTCGAGC | 6840 |
| CGATCCGGCT GCAG | 6854 |

(2) INFORMATION FOR SEQ ID NO: 8:

(i) SEQUENCE CHARACTERISTICS:
        (A) LENGTH: 240 amino acids

```
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 8:

Val Ile Val Ala Glu His Leu Val Lys Glu Phe Arg Leu Ala Glu Arg
1               5                   10                  15

Glu Pro Gly Leu Leu Gly Ser Leu Ser Thr Leu Leu Thr Arg Arg Tyr
                20                  25                  30

Arg Val Val Arg Ala Val Asp Asp Val Ser Phe Glu Ile Pro Ala Gly
            35                  40                  45

Thr Lys Thr Ala Tyr Ile Gly Ala Asn Gly Ala Gly Lys Ser Thr Thr
    50                  55                  60

Ile Lys Met Leu Thr Gly Ile Met Thr Pro Thr Ser Gly Arg Cys Thr
65                  70                  75                  80

Val Ala Gly Leu Glu Pro Tyr Arg His Arg Gln Arg Asn Ala Arg Thr
                85                  90                  95

Ile Gly Val Val Phe Gly Gln Arg Ser Gln Leu Trp Trp Asp Leu Ser
            100                 105                 110

Val Pro Asp Ser Phe Arg Ile Leu Arg Arg Ile Tyr Asp Ile Pro Gly
        115                 120                 125

Pro Val Tyr Arg Arg Asn Leu Ala Leu Phe Arg Asp Leu Leu Asp Ile
    130                 135                 140

Asp Ala Leu Gly Ser Thr Pro Val Arg Gln Leu Ser Leu Gly Gln Arg
145                 150                 155                 160

Met Arg Ala Glu Ile Ala Ala Ser Leu Leu His Asp Pro Ala Val Leu
                165                 170                 175

Phe Trp Asp Glu Pro Thr Ile Gly Leu Asp Met Val Leu Lys Asp Ala
            180                 185                 190

Val Arg Arg Leu Val Asn Arg Ala His Arg Glu Leu Gly Thr Thr Val
        195                 200                 205

Val Leu Thr Ser His Asp Ile Ala Asp Ile Ala Ala Ile Cys Asp Ser
    210                 215                 220

Ala Leu Val Val Asp Gln Gly Arg Val Val His Gln Gly Thr Leu Gln
225                 230                 235                 240

(2) INFORMATION FOR SEQ ID NO: 9:

(i) SEQUENCE CHARACTERISTICS:
        (A) LENGTH: 429 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 9:

Met Thr Gly Leu Arg Gln Thr Gln His Leu Ala Arg Glu Ala Arg His
1               5                   10                  15

Leu Ala Pro Gly Ala Ser Glu Glu Ala Val His Gly Arg Arg Val Phe
                20                  25                  30

Ala Glu Gly Arg Gly Pro Val Leu Thr Asp Leu Asp Gly Asn Gln Tyr
            35                  40                  45

Leu Asp Phe Ala Ala Gly Thr Leu Thr Gln Ser Leu Gly His Gly His
    50                  55                  60

Pro Glu Val Val Glu Ala Leu Thr Thr Gln Ala Arg Arg Leu Trp Asn
```

```
            65                   70                  75                  80
        Val His Asp Ser Ala Thr Pro Asp Arg Ala Gly Leu Leu Glu Leu Leu
                         85                  90                  95
        Ala Arg Leu Leu Pro Glu Gln Leu Asp Thr Tyr Ala Phe Phe Ser Thr
                        100                 105                 110
        Gly Ala Glu Val Val Glu Ala Ala Leu Arg Val Val Gln Ala Thr Ala
                        115                 120                 125
        Ala Pro Gly Arg Asn Arg Ile Cys Ala Leu Arg His Gly Phe His Gly
                        130                 135                 140
        Lys Thr Met Gly Ala Arg Met Leu Val His Trp Asp Ile Gly His Gln
        145                 150                 155                 160
        Ala Phe Ser Gly Asn Ser Val Leu Ala Thr Ala Pro Thr Gly Tyr Arg
                        165                 170                 175
        Cys Pro Leu Gly Leu Glu Tyr Pro Ser Cys Asp Val Arg Cys Ala Thr
                        180                 185                 190
        Leu Val Arg Arg His Ile Ala Glu Lys Pro Asn Val Ser Ala Leu Val
                        195                 200                 205
        Phe Glu Pro Val Leu Gly Ala Ala Gly Val Ile Val Pro Pro Pro Gly
                        210                 215                 220
        Tyr Trp Glu Arg Ile Ala Gly Ala Cys Arg Asp Gly Val Leu Leu
        225                 230                 235                 240
        Val Ala Asp Glu Val Leu Thr Gly Gly Arg Thr Gly Ala Phe Leu
                        245                 250                 255
        Ala Ser Glu Leu Phe Gly Ile Glu Pro Asp Leu Ala Met Leu Ser Lys
                        260                 265                 270
        Gly Thr Ala Ser Gly Phe Pro Phe Ala Val Leu Ala Gly Arg Ala Glu
                        275                 280                 285
        Ala Ala Gln Ala Gly Gly His Pro Gly Ala Tyr Ala Ser Thr Tyr
                        290                 295                 300
        Ala Ser Asn Pro Leu Gly Ile Ala Ala Ala Arg Ala Thr Leu Glu Val
        305                 310                 315                 320
        Val Glu Arg Asp Arg Leu Ile Asp Arg Val Arg Val Leu Gly Glu Leu
                        325                 330                 335
        Ile Gln Glu Arg Leu Arg Ala Leu Glu Ser Arg Phe Pro Gln Leu Gly
                        340                 345                 350
        Gln Val Arg Gly Leu Gly Leu Leu Trp Gly Leu Glu Phe Val Thr Asp
                        355                 360                 365
        Ala Val Gly Arg Ala Pro Ala Pro Glu Thr Ala Arg Ala Val Tyr Thr
                        370                 375                 380
        Thr Ala Leu Asp Leu Gly Leu Arg Thr Ser Leu Gly Gly His Ile Leu
        385                 390                 395                 400
        Arg Leu Ala Pro Pro Phe Thr Leu Asp Glu Ala Leu Leu Asp Glu Gly
                        405                 410                 415
        Leu Arg Leu Leu Glu Thr Ala Val Glu Arg Val Ile Ala
                        420                 425
```

(2) INFORMATION FOR SEQ ID NO: 10:

(i) SEQUENCE CHARACTERISTICS:
        (A) LENGTH: 355 amino acids
        (B) TYPE: amino acid
        (C) STRANDEDNESS: <Unknown>
        (D) TOPOLOGY: linear (ii) MOLECULE TYPE: protein -continued (xi) SEQUENCE DESCRIPTION: SEQ ID NO: 10:

| Val | Lys | Ala | Leu | Val | Leu | Ala | Gly | Gly | Thr | Gly | Ser | Arg | Leu | Arg | Pro |
| 1 | | | | 5 | | | | | 10 | | | | | 15 | |

| Phe | Thr | His | Thr | Ala | Ala | Lys | Gln | Leu | Leu | Pro | Ile | Ala | Asn | Lys | Pro |
| | | | 20 | | | | | 25 | | | | | 30 | | |

| Val | Leu | Phe | Tyr | Ala | Leu | Glu | Ser | Leu | Ala | Ala | Gly | Val | Arg | Glu |
| | | | 35 | | | | 40 | | | | | 45 | | |

| Ala | Gly | Val | Val | Gly | Ala | Tyr | Gly | Arg | Glu | Ile | Arg | Glu | Leu | Thr |
| | 50 | | | | 55 | | | | | 60 | | | | |

| Gly | Asp | Gly | Thr | Ala | Phe | Gly | Leu | Arg | Ile | Thr | Tyr | Leu | His | Gln | Pro |
| 65 | | | | 70 | | | | | 75 | | | | | 80 | |

| Arg | Pro | Leu | Gly | Leu | Ala | His | Ala | Val | Arg | Ile | Ala | Arg | Gly | Phe | Leu |
| | | | 85 | | | | | 90 | | | | | 95 | | |

| Gly | Asp | Asp | Asp | Phe | Leu | Leu | Tyr | Leu | Gly | Asp | Asn | Tyr | Leu | Pro | Gln |
| | | | 100 | | | | | 105 | | | | | 110 | | |

| Gly | Val | Thr | Asp | Phe | Ala | Arg | Gln | Ser | Ala | Ala | Asp | Pro | Ala | Ala | Ala |
| | | | 115 | | | | | 120 | | | | | 125 | | |

| Arg | Leu | Leu | Leu | Thr | Pro | Val | Ala | Asp | Pro | Ser | Ala | Phe | Gly | Val | Ala |
| | 130 | | | | 135 | | | | | 140 | | | | | |

| Glu | Val | Asp | Ala | Asp | Gly | Asn | Val | Leu | Arg | Leu | Glu | Glu | Lys | Pro | Asp |
| 145 | | | | | 150 | | | | | 155 | | | | | 160 |

| Val | Pro | Arg | Ser | Ser | Leu | Ala | Leu | Ile | Gly | Val | Tyr | Ala | Phe | Ser | Pro |
| | | | | 165 | | | | | 170 | | | | | 175 | |

| Ala | Val | His | Glu | Ala | Val | Arg | Ala | Ile | Thr | Pro | Ser | Ala | Arg | Gly | Glu |
| | | | 180 | | | | | 185 | | | | | 190 | | |

| Leu | Glu | Ile | Thr | His | Ala | Val | Gln | Trp | Met | Ile | Asp | Arg | Gly | Leu | Arg |
| | | 195 | | | | | 200 | | | | | 205 | | | |

| Val | Arg | Ala | Glu | Thr | Thr | Thr | Arg | Pro | Trp | Arg | Asp | Thr | Gly | Ser | Ala |
| | 210 | | | | | 215 | | | | | 220 | | | | |

| Glu | Asp | Met | Leu | Glu | Val | Asn | Arg | His | Val | Leu | Asp | Gly | Leu | Glu | Gly |
| 225 | | | | | 230 | | | | | 235 | | | | | 240 |

| Arg | Ile | Glu | Gly | Lys | Val | Asp | Ala | His | Ser | Thr | Leu | Val | Gly | Arg | Val |
| | | | | 245 | | | | | 250 | | | | | 255 | |

| Arg | Val | Ala | Glu | Gly | Ala | Ile | Val | Arg | Gly | Ser | His | Val | Val | Gly | Pro |
| | | | 260 | | | | | 265 | | | | | 270 | | |

| Val | Val | Ile | Gly | Ala | Gly | Ala | Val | Val | Ser | Asn | Ser | Ser | Val | Gly | Pro |
| | | 275 | | | | | 280 | | | | | 285 | | | |

| Tyr | Thr | Ser | Ile | Gly | Glu | Asp | Cys | Arg | Val | Glu | Asp | Ser | Ala | Ile | Glu |
| | 290 | | | | | 295 | | | | | 300 | | | | |

| Tyr | Ser | Val | Leu | Leu | Arg | Gly | Ala | Gln | Val | Glu | Gly | Ala | Ser | Arg | Ile |
| 305 | | | | | 310 | | | | | 315 | | | | | 320 |

| Glu | Ala | Ser | Leu | Ile | Gly | Arg | Gly | Ala | Val | Val | Gly | Pro | Ala | Pro | Arg |
| | | | | 325 | | | | | 330 | | | | | 335 | |

| Leu | Pro | Gln | Ala | His | Arg | Leu | Val | Ile | Gly | Asp | His | Ser | Lys | Val | Tyr |
| | | | 340 | | | | | 345 | | | | | 350 | | |

| Leu | Thr | Pro |
| | | 355 |

(2) INFORMATION FOR SEQ ID NO: 11:

(i) SEQUENCE CHARACTERISTICS:
      (A) LENGTH: 325 amino acids
      (B) TYPE: amino acid
      (C) STRANDEDNESS: <Unknown>
      (D) TOPOLOGY: linear (ii) MOLECULE TYPE: protein (xi) SEQUENCE DESCRIPTION: SEQ ID NO: 11:

```
Met Thr Thr Thr Ile Leu Val Thr Gly Gly Ala Gly Phe Ile Arg Ser
1               5                   10                  15

Ala Tyr Val Arg Arg Leu Leu Ser Pro Gly Ala Pro Gly Gly Val Ala
            20                  25                  30

Val Thr Val Leu Asp Lys Leu Thr Tyr Ala Gly Ser Leu Ala Arg Leu
        35                  40                  45

His Ala Val Arg Asp His Pro Gly Leu Thr Phe Val Gln Gly Asp Val
50              55                  60

Cys Asp Thr Ala Leu Val Asp Thr Leu Ala Ala Arg His Asp Asp Ile
65                  70                  75                  80

Val His Phe Ala Ala Glu Ser His Val Asp Arg Ser Ile Thr Asp Ser
                85                  90                  95

Gly Ala Phe Thr Arg Thr Asn Val Leu Gly Thr Gln Val Leu Leu Asp
            100                 105                 110

Ala Ala Leu Arg His Gly Val Arg Thr Phe Val His Val Ser Thr Asp
        115                 120                 125

Glu Val Tyr Gly Ser Leu Pro His Gly Ala Ala Ala Glu Ser Asp Pro
130                 135                 140

Leu Leu Pro Thr Ser Pro Tyr Ala Ala Ser Lys Ala Ala Ser Asp Leu
145                 150                 155                 160

Met Ala Leu Ala His His Arg Thr His Gly Leu Asp Val Arg Val Thr
                165                 170                 175

Arg Cys Ser Asn Asn Phe Gly Pro His Gln His Pro Glu Lys Leu Ile
            180                 185                 190

Pro Arg Phe Leu Thr Ser Leu Leu Ser Gly Gly Thr Val Pro Leu Tyr
        195                 200                 205

Gly Asp Gly Arg His Val Arg Asp Trp Leu His Val Asp Asp His Val
210                 215                 220

Arg Ala Val Glu Leu Val Arg Val Ser Gly Arg Pro Gly Glu Ile Tyr
225                 230                 235                 240

Asn Ile Gly Gly Gly Thr Ser Leu Pro Asn Leu Glu Leu Thr His Arg
                245                 250                 255

Leu Leu Ala Leu Cys Gly Ala Gly Pro Glu Arg Ile Val His Val Glu
            260                 265                 270

Asn Arg Lys Gly His Asp Arg Arg Tyr Ala Val Asp His Ser Lys Ile
        275                 280                 285

Thr Ala Glu Leu Gly Tyr Arg Pro Arg Thr Asp Phe Ala Thr Ala Leu
290                 295                 300

Ala Asp Thr Ala Lys Trp Tyr Glu Arg His Glu Asp Trp Trp Arg Pro
305                 310                 315                 320

Leu Leu Ala Ala Thr
                325
```

(2) INFORMATION FOR SEQ ID NO: 12:

(i) SEQUENCE CHARACTERISTICS:
        (A) LENGTH: 345 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 12:

```
Met Thr Met Arg Leu Ala Asp Ile Ala Ala Arg Ala Gly Val Ser Lys
1               5                   10                  15

Ala Thr Val Ser Arg Val Leu Asn Gly Ala Arg Gly Val Ala Thr Gly
                20                  25                  30

Thr Arg Asp Ser Val Leu Thr Ala Leu Asp Ala Leu Gly Tyr Glu Gln
            35                  40                  45

Pro Ala Arg Gln Arg Arg Ala Glu Leu Val Gly Leu Val Thr Pro Glu
        50                  55                  60

Leu Asp Asn Pro Phe Phe Pro Ala Leu Ala Gln Val Met Gly Gln Ala
65                  70                  75                  80

Leu Thr Arg Gln Gly Tyr Thr Pro Val Leu Ala Thr Gln Thr Pro Gly
                85                  90                  95

Gly Ser Thr Glu Asp Glu Leu Thr Glu Met Leu Val Asp Arg Gly Val
                100                 105                 110

Ser Gly Ile Ile Phe Val Ser Gly Leu His Ala Asp Thr Thr Ala Glu
            115                 120                 125

Thr Gly Arg Tyr Gly Arg Leu His Glu Arg Gln Val Pro Phe Val Leu
        130                 135                 140

Val Asn Gly Phe Ser Pro Arg Ile Glu Ala Pro Phe Val Ser Pro Asp
145                 150                 155                 160

Asp Arg Ala Ala Met Arg Leu Ala Val Ala His Leu Ala Glu Leu Gly
                165                 170                 175

His Glu Arg Val Gly Leu Ala Val Gly Pro Ala Arg Phe Val Pro Val
                180                 185                 190

Gln Arg Lys Ile Glu Gly Phe Arg Ala Gly Val Arg Glu His Leu Gly
            195                 200                 205

Val Ser Ala Arg Glu Ser Glu Glu Leu Val Gln His Ser Leu Phe Ser
210                 215                 220

Leu Glu Gly Gly Gln Ala Ala Ser Ala Leu Ile Asp Leu Gly Cys
225                 230                 235                 240

Thr Ala Val Met Cys Ala Ser Asp Met Met Ala Leu Gly Ala Val Arg
                245                 250                 255

Ala Ala Arg Arg Arg Gly Leu Thr Val Pro Gly Asp Ile Ser Val Val
            260                 265                 270

Gly Phe Asp Asp Ser Pro Leu Met Ala Phe Thr Asp Pro Pro Leu Thr
        275                 280                 285

Thr Ile Arg Gln Pro Val Lys Ala Met Gly Gln Val Ala Val Asp Ala
    290                 295                 300

Leu Leu Glu Glu Met Ser Gly Thr Pro Pro Arg Thr Glu Phe Val
305                 310                 315                 320

Phe Met Pro Glu Leu Val Val Arg Gly Ser Thr Ala Ala Gly Pro Arg
                325                 330                 335

Gly Gly Arg Arg Pro Ala His Gly Arg
                340                 345
```

(2) INFORMATION FOR SEQ ID NO: 13:

(i) SEQUENCE CHARACTERISTICS:
        (A) LENGTH: 393 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 13:

```
Met Arg Arg Gly Ile Ala Ala Thr Ala Leu Phe Ala Ala Val Ala Met
  1               5                  10                  15

Thr Ala Ser Ala Cys Gly Gly Asp Asn Gly Gly Ser Gly Thr Asp
             20                  25                  30

Ala Gly Gly Thr Glu Leu Ser Gly Thr Val Thr Phe Trp Asp Thr Ser
             35                  40                  45

Asn Glu Ala Glu Lys Ala Thr Tyr Gln Ala Leu Ala Glu Gly Phe Glu
         50                  55                  60

Lys Glu His Pro Lys Val Asp Val Lys Tyr Val Asn Val Pro Phe Gly
 65                  70                  75                  80

Glu Ala Asn Ala Lys Phe Lys Asn Ala Ala Gly Gly Asn Ser Gly Ala
                 85                  90                  95

Pro Asp Val Met Arg Thr Glu Val Ala Trp Val Ala Asp Phe Ala Ser
                100                 105                 110

Ile Gly Tyr Leu Ala Pro Leu Asp Gly Thr Pro Ala Leu Asp Asp Gly
            115                 120                 125

Ser Asp His Leu Pro Gln Gly Gly Ser Thr Arg Tyr Glu Gly Lys Thr
130                 135                 140

Tyr Ala Val Pro Gln Val Ile Asp Thr Leu Ala Leu Phe Tyr Asn Lys
145                 150                 155                 160

Glu Leu Leu Thr Lys Ala Gly Val Glu Val Pro Gly Ser Leu Ala Glu
                165                 170                 175

Leu Lys Thr Ala Ala Glu Ile Thr Glu Lys Thr Gly Ala Ser Gly
                180                 185                 190

Leu Tyr Cys Gly Ala Thr Thr Arg Thr Trp Phe Leu Pro Tyr Leu Tyr
            195                 200                 205

Gly Glu Gly Gly Asp Leu Val Asp Glu Lys Asn Lys Thr Val Thr Val
        210                 215                 220

Asp Asp Glu Ala Gly Val Arg Ala Tyr Arg Val Ile Lys Asp Leu Val
225                 230                 235                 240

Asp Ser Lys Ala Ala Ile Thr Asp Ala Ser Asp Gly Trp Asn Asn Met
                245                 250                 255

Gln Asn Ala Phe Lys Ser Gly Lys Val Ala Met Met Val Asn Gly Pro
            260                 265                 270

Trp Ala Ile Glu Asp Val Lys Ala Gly Ala Arg Phe Lys Asp Ala Gly
        275                 280                 285

Asn Leu Gly Val Ala Pro Val Pro Ala Gly Ser Ala Gln Gly Ser
    290                 295                 300

Pro Gln Gly Gly Trp Asn Leu Ser Val Tyr Ala Gly Ser Lys Asn Leu
305                 310                 315                 320

Asp Ala Ser Tyr Ala Phe Val Lys Tyr Met Ser Ser Ala Lys Val Gln
            325                 330                 335

Gln Gln Thr Thr Glu Lys Leu Ser Leu Leu Pro Thr Arg Thr Ser Val
            340                 345                 350

Tyr Glu Val Pro Ser Val Ala Asp Asn Glu Met Val Lys Phe Phe Lys
            355                 360                 365

Pro Ala Val Asp Lys Ala Val Glu Arg Pro Trp Ile Ala Glu Gly Asn
370                 375                 380

Ala Leu Phe Glu Pro Ile Arg Leu Gln
385                 390
```

ISOLATION OF BIOSYNTHESIS GENES FOR PSEUDO-OLIGOSACCHARIDES FROM *STREPTOMYCES GLAUCESCENS* GLA.O, AND THEIR USE

This application is a division of U.S. application Ser. No. 09/194,905 filed Dec. 29, 1998, now U.S. Pat. No. 6,306,627, Oct. 23, 2001, which claims priority to PCT/EP97/02826 filed May 30, 1997 and DE 19622783.6 filed Jul. 7, 1996.

The present invention relates to the isolation of genes which encode enzymes for the biosynthesis of α-amylase inhibitors, so-called pseudo-oligosaccharides. The genes concerned are, in particular, genes from the *Streptomycetes* strain *Streptomyces glaucescens* GLA.O (DSM 40716). In addition, this present patent describes the use of these genes for producing acarbose and homologous substances with the aid of *Streptomyces glaucescens* GLA.O, the heterologous expression of these genes in other strains which produce pseudo-oligosaccharides (e.g. *Actinoplanes* sp SE50/100) for the purpose of increasing and stabilizing production, and also their heterologous expression in other microorganisms such as *E. coli, Bacillus subtilis, Actinomycetales*, such as *Streptomyces, Actinoplanes, Ampullariella* and *Streptoporangium* strains, *Streptomyces hygroscopicus* var. *limoneus* and *Streptomyces glaucescens*, and also biotechnologically relevant fungi (e.g. *Aspergillus niger* and *Penicillium chrysogenum*) and yeasts (e.g. *Saccharomyces cerevisiae*). The invention also relates to homologous genes in other microorganisms and to methods for isolating them.

*Streptomyces glaucescens* GLA.O produces the two antibiotics hydroxystreptomycin (Hütter (1967) Systematik der Streptomyceten (Taxonomy of the *Streptomycetes*). Basel, Karger Verlag) and tetracenomycin (Weber et al. (1979) Arch. Microbiol. 121: 111–116). It is known that *streptomycetes* are able to synthesize structurally varied natural products. However, the conditions under which these compounds are produced are frequently unknown, or else the substances are only produced in very small quantities and not detected.

The α-amylase inhibitor acarbose has been isolated from a variety of *Actinoplanes* strains (SE50, SE82 and SE18) (Schmidt et al. (1977) Naturwissenschaften 64: 535–536). This active substance was discovered in association with screening for α-amylase inhibitors from organisms of the genera *Actinoplanes, Ampullariella* and *Streptosporangium*. Acarbose is pseudotetrasaccharide which is composed of an unusual unsaturated cyclitol unit to which an amino sugar, i.e. 4,6-dideoxy-4-amino-D-glucopyranose, is bonded. Additional α-1,4-glycosidically linked D-glucopyranose units can be bonded to the amino sugar. Thus, acarbose, for example, contains two further molecules of D-glucose. The producing strain synthesizes a mixture of pseudo-oligosaccharide products which possess sugar side chains of different lengths (Schmidt et al. (1977) Naturwissenschaften 64: 535–536). The acarbose cyclitol residue is identical to the compound valienamine, which is a component of the antibiotic validamycin A (Iwasa et al. (1979) J. Antibiot. 32: 595–602) from *Streptomyces hygroscopicus* var. *limoneus*.

Acarbose can be produced by fermentation using an *Actinoplanes* strain and has achieved great economic importance as a therapeutic agent for diabetics. While *Actinoplanes* synthesizes a mixture of α-amylase inhibitor products, it is only the compound having the relative molecular weight of 645.5 (acarviosin containing 2 glucose units (Truscheit (1984) VIIIth International Symposium on Medicinal Chemistry, Proc. Vol. 1. Swedish Academy of Pharmaceutical Sciences, Stockholm, Sweden), which is employed under the generic name of acarbose. The fermentation conditions are selected to ensure that acarbose is the main product of the fermentation. Alternatives are to use particular selectants and strains in which acarbose is formed as the main product or to employ purification processes for achieving selective isolation (Truscheit (1984) VIIIth International Symposium on Medicinal Chemistry, Proc. Vol. 1. Swedish Academy of Pharmaceutical Sciences, Stockholm, Sweden). It is also possible to transform the product mixture chemically in order, finally, to obtain the desired product acarbose.

In contrast to the genus *Streptomyces*, the genus *Actinoplanes* has not so far been investigated intensively from the genetic point of view. Methods which were established for the genus *Streptomyces* are not transferable, or are not always transferable, to the genus *Actinoplanes*. In order to use molecular biological methods to optimize acarbose production in a purposeful manner, the genes for acarbose biosynthesis have to be isolated and characterized. In this context, the possibility suggests itself of attempting to set up a host/vector system for *Actinoplanes* sp. However, this is very tedious and elaborate owing to the fact that studies on *Actinoplanes* have been relatively superficial.

The invention described in the present patent application achieves the object of cloning the biosynthesis genes for acarbose and homologous pseudo-oligosaccharides, with these genes being cloned from *Streptomyces glaucescens* GLA.O, which is a *streptomycete* which has been thoroughly investigated genetically (Crameri et al. (1983) J. Gen. Microbiol. 129: 519–527; Hintermann et al. (1984) Mol. Gen. Genet. 196: 513–520; Motamedi and Hutchinson (1987) PNAS USA 84: 4445–4449; Geistlich et al. (1989) Mol. Microbiol. 3: 1061–1069) and which, surprisingly, is an acarbose producer. In starch-containing medium, *Streptomyces glaucescens* GLA.O produces pseudo-oligosaccharides having the molecular weights 645, 807 and 970.

Part of the subject matter of the invention is, therefore, the isolation of the corresponding biosynthesis genes from *Streptomyces glaucescens* GLA.O and their use for isolating the adjoining DNA regions in order to complete the gene cluster of said biosynthesis genes.

The isolation of the genes for biosynthesizing pseudo-oligosaccharides, and the characterization of these genes, are of great importance for achieving a better understanding of the biosynthesis of the pseudo-oligosaccharides and its regulation. This knowledge can then be used to increase the productivity of the *Streptomyces glaucescens* GLA.O strain with regard to acarbose production by means of established classical and molecular biological methods. In addition to this, the entire gene cluster which encodes the synthesis of the pseudo-oligosaccharides, or individual genes from this gene cluster, can also be expressed in other biotechnologically relevant microorganisms in order to achieve a further increase in, or a simplification of, the preparation of pseudo-oligosaccharides such as acarbose. Specific modification of the biosynthesis genes can also be used to prepare a strain which exclusively produces acarbose having a molecular weight of 645. Since the genes for biosynthesizing antibiotics are always present in clusters and are often very strongly conserved (Stockmann and Piepersberg (1992) FEMS Microbiol. Letters 90: 185–190; Malpartida et al. (1987) Nature 314:642–644), the *Streptomyces glaucescens* GLA.O genes can also be used as a probe for isolating the acarbose-encoding genes from *Actinoplanes* sp., for example. The expression of regulatory genes, or of genes which encode limiting steps in the biosynthesis, can result in productivity in *Streptomyces glaucescens* GLA.O, *Actinoplanes* sp. or corresponding producer strains being increased. An increase in productivity can also be achieved by switching off (knocking out or mutagenizing) those acarbose biosynthesis genes which have an inhibitory effect in the biosynthesis.

One possible strategy for cloning antibiotic biosynthesis genes which have not previously been isolated is that of using gene-specific probes (Stockmann and Piepersberg (1992) FEMS Microbiol. Letters 90: 185–190; Malpartida et al. (1987) Nature 314:642–644). These probes can be DNA fragments which are $P^{32}$-labeled or labeled in some other way; otherwise, the appropriate genes can be amplified directly from the strains to be investigated using degenerate PCR primers and isolated chromosomal DNA as the template.

The latter method has been employed in the present study. Pseudo-oligosaccharides such as acarbose contain a 4,6-deoxyglucose building block as a structural element. The enzyme dTDP-glucose 4,6-dehydratase is known to be involved in the biosynthesis of 4,6-deoxyglucose (Stockmann and Piepersberg (1992) FEMS Microbiol, Letters 90: 185–190). Since deoxysugars are a frequent constituent of natural products and antibiotics, this enzyme may possibly be a means for isolating the corresponding antibiotic biosynthesis genes. Since these genes are always present as clusters, it is sufficient to initially isolate one gene; the isolation and characterization of the adjoining DNA regions can then be undertaken subsequently.

For example a dTDP-glucose 4,6-dehydratase catalyzes a step in the biosynthesis of hydroxystreptomycin in *Streptomyces glaucescens* GLA.O (Retzlaff et al. (1993) Industrial Microorganisms. Basic and applied molecular genetics ASM, Washington D.C., USA). Further dTDP-glucose 4,6-dehydratases have been isolated from other microorganisms, for example from *Streptomyces griseus* (Pissowotzki et al. (1991) Mol. Gen. Genet. 231: 113–123), *Streptomyces fradiae* (Merson-Davies and Cundcliffe (1994) Mol. Microbiol. 13: 349–355) and *Streptomyces violaceoruber* (Bechthold, et al. (1995) Mol. Gen. Genet. 248: 610–620).

It was consequently possible to deduce the sequences for the PCR primers for amplifying a dTDP-glucose 4,6-dehydratase from the amino acid sequences of already known biosynthesis genes. For this, conserved regions in the protein sequences of these enzymes were selected and the amino acid sequences were translated into a nucleic acid sequence in accordance with the genetic code. The protein sequences were taken from the EMBL and Genbank databases. The following sequences were used: *Streptomyces griseus*; accession number: X62567 gene: strE (dated Oct. 30, 1993); *Streptomyces violaceoruber*; accession number: L37334 gene: graE (dated Apr. 10, 1995); *Saccharopolyspora etythraea*; accession number: L37354 gene: gdh (dated Nov. 9, 1994). A large number of possible primer sequences are obtained as a result of the degeneracy of the genetic code. The fact that *streptomycetes* usually contain a G or C in the third position of a codon (Wright and Bibb (1992) gene 113: 55–65) reduces the number of primers to be synthesized. These primer mixtures can then be used to carry out a PCR amplification with the DNA from strains to be investigated, with the amplification ideally leading to an amplified DNA fragment. In the case of highly conserved proteins, this fragment is of a predictable length which ensues from the distance between the primers in the nucleic acid sequence of the corresponding gene. However, an experimental mixture of this nature does not inevitably have to result in an amplificate. The primers may be too unspecific and amplify a very large number of fragments; alternatively, no PCR product is obtained if there are no complementary binding sites in the chromosome for the PCR primers which have been prepared.

The investigation of the *streptomycete* strain *Streptomyces glaucescens* GLA.O resulted in an amplified DNA fragment (acbD) which had the expected length of 550 bp. Further investigation showed that, besides containing a dTDP-glucose 4,6-dehydratase gene for biosynthesizing hydroxystreptomycin, this strain surprisingly contains a second dTDP-glucose 4,6-dehydratase gene for biosynthesizing pseudo-oligosaccharides such as acarbose. While the two genes exhibit a high degree of homology, they are only 65% identical at the amino acid level.

The acbD probe (see Example 2 and Table 2A) was used to isolate, from *Streptomyces glaucescens* GLA.O, a 6.8 kb Pstl DNA fragment which encodes a variety of genes (acbA, acbB, acdC, acbD, acbE and acbF) which are involved in the biosynthesis of the pseudo-oligosaccharides.

Deleting the acbBCD genes (aminotransferase, acbB, dTDP-glucose synthase, acbC, dTDP-glucose 4,6-dehydratase, acbD, see Example 6) resulted in the production of a mutant of *Streptomyces glaucescens* GLA.O which no longer produces any pseudo-oligosaccharides in the production medium. The involvement of the acbBCD genes in the synthesis of pseudo-oligosaccharides was therefore verified by deleting the corresponding loci.

The two genes, i.e. dTDP-glucose synthase and dTDP-glucose 4,6-dehydratase, ought to be involved in the biosynthesis of the deoxysugar of the pseudo-oligosaccharides, as can be concluded from the function of thoroughly investigated homologous enzymes (see above). The aminotransferase (encoded by the acbB gene) is probably responsible for transferring the amino group either to the sugar residue or to the cyclitol residue. By analyzing the protein sequence of acbB, an amino acid motif was found which is involved in binding pyridoxal phosphate. This motif is typical of class III aminotransferases (EC 2.6.1.11; EC 2.6.1.13; EC 2.6.1.18; EC 2.6.1.19; EC 2.6.1.62; EC 2.6.1.64; EC 5.4.3.8). The precise enzymic function of acbB can only be elucidated by further investigation of the biosynthesis of the pseudo-oligosaccharides. acbE encodes a transcription-regulating protein which exhibits a great deal of similarity to DNA-binding proteins which possess a helix-turn-helix motif (e.g. *Bacillus subtilis* DegA, P37947: Swiss-Prot database). Thus, the transcription activator CcpA from *Bacillus subtilis* inhibits the formation of α-amylase in the presence of glucose, for example (Henkin et al. (1991) Mol. Microbiol. 5: 575–584). Other representatives of this group are proteins which recognize particular sugar building blocks and are able to exhibit a positive or negative effect on the biosynthesis of metabolic pathways. The biosynthesis of the pseudo-oligosaccharides is also regulated in *Streptomyces glaucescens* GLA.O. It was only previously possible to demonstrate the synthesis of pseudo-oligosaccharides on starch-containing media. While this method indicated that AcbE might be responsible for regulating pseudo-oligosaccharide synthesis, the precise mechanism is still not known. However, molecular biological methods can now be used to modify the gene specifically in order to obtain an increased rate of pseudo-oligosaccharide biosynthesis. Furthermore, the DNA site at which acbE binds can be identified by means of so-called gel shift assays (Miwa et al. (1994) Microbiology 140: 2576–2575). An increase in the rate at which acarbose is biosynthesized can be achieved after identifying and then modifying the promoters and other regulatory DNA regions which are responsible for the transcription of the pseudo-oligosaccharide genes.

At present, the function of acbF is still not definitely known. The corresponding gene product exhibits homologies with sugar-binding proteins such as the sugar-binding protein from *Streptococcus mutans* (MsmE; Q00749: Swissprot database), making it probable that it is involved in the biosynthesis of the pseudo-oligosaccharides. The gene product of the acbA gene exhibits homologies with known bacterial ATP-binding proteins (e.g. from *Streptomyces peucitus* DrrA, P32010: SwissProt database). The AcbA protein possesses the typical ATP/GTP binding motif, i.e. the so-called P loop. These proteins constitute an important component of so-called ABC transporters, which are involved in the active transport of metabolites at biological membranes (Higgins (1995) Cell 82: 693–696). Accordingly, AcbA could be responsible for exporting pseudo-oligosaccharides out of the cell or be involved in importing sugar building blocks for biosynthesizing α-amylase inhibitors such as maltose.

All *streptomycete* genes for biosynthesizing secondary metabolites which have so far been analyzed are arranged in a cluster. For this reason, it is to be assumed that the acarbose biosynthesis genes according to the application are also arranged in such a gene cluster. The remaining genes which are relevant for pseudo-oligosaccharide biosynthesis can therefore also be isolated by isolating the DNA regions which adjoin the 6.8 kb PstI DNA fragment according to the invention. As has also already been mentioned above, it is readily possible to isolate homologous gene clusters from microorganisms other than *Streptomyces glaucescens* GLA.O.

The invention therefore relates to a recombinant DNA molecule which comprises genes for biosynthesizing acarbose and homologous pseudo-oligosaccharides, in particular a recombinant DNA molecule in which individual genes are arranged, with respect to their direction of transcription and order, as depicted in FIG. 3 and/or which exhibits a restriction enzyme cleavage site pattern as depicted in FIG. 3, and, preferably, to a recombinant DNA molecule which (a) comprises a DNA sequence according to Table 4, or parts thereof;

(b) comprises a DNA sequence which is able to hybridize, under stringent conditions, with the DNA molecule according to (a), or parts thereof; or (c) comprises a DNA sequence which, because of the degeneracy of the genetic code, differs from the DNA molecules according to (a) and (b) but which permits the expression of the proteins which can be correspondingly expressed using the DNA molecule according to (a) and (b), or parts thereof.

The invention furthermore relates to a recombinant DNA molecule which comprises the acbA gene, in particular which is characterized in that it comprises the DNA sequence of nucleotides 1 to 720 according to Table 4, or parts thereof; to a recombinant DNA molecule which comprises the acbB gene, in particular which is characterized in that it comprises the DNA sequence of nucleotides 720 to 2006 according to Table 4, or parts thereof; to a recombinant DNA molecule which comprises the acbC gene, in particular which is characterized in that it comprises the DNA sequence of nucleotides 2268 to 3332 according to Table 4, or parts thereof; to a recombinant DNA molecule which comprises the acbD gene, in particular which is characterized in that it comprises the DNA sequence of nucleotides 3332 to 4306 according to Table 4, or parts thereof; to a recombinant DNA molecule which comprises the acbE gene, in particular which is characterized in that it comprises the DNA sequence of nucleotides 4380 to 5414 according to Table 4, or parts thereof; and to a recombinant DNA molecule which comprises the acbF gene, in particular which is characterized in that it comprises the DNA sequence of nucleotides 5676 to 6854 according to Table 4, or parts thereof.

The invention furthermore relates to oligonucleotide primers for the PCR amplification of a recombinant DNA molecule which is as described above and which comprises genes for biosynthesizing acarbose and homologous pseudo-oligosaccharides, with the primers having, in particular, the sequence according to Table 1.

The invention furthermore relates to a vector which comprises a recombinant DNA molecule which comprises a DNA molecule as described in the penultimate and prepenultimate paragraphs, in particular which is characterized in that the vector is an expression vector and said DNA molecule is linked operatively to a promoter sequence, with the vector preferably being being suitable for expression in host organisms which are selected from the group consisting of *E. coli, Bacillus subtilis, Actinomycetales*, such as *Streptomyces, Actinoplanes, Ampullariella* and *Streptosporangium* strains, *Streptomyces hygroscopicus* var. *limoneus, Streptomyces glaucescens* and also biotechnologically relevant fungi (e.g. *Aspergillus niger, Penicillium chrysogenum*) and yeasts (e.g. *Saccharomyces cerevisiae*), with *Streptomyces glaucescens* GLA.O or *Actinoplanes* sp. being very particularly preferred. Since the operative linkage of said DNA molecule to promoter sequences of the vector is only one preferably embodiment of the invention, it is also possible for expression to be achieved using promoter sequences which are endogenous in relation to the DNA molecule, e.g. the promoters which are in each case natural, or the natural promoters which have been mutated with regard to optimizing the acarbose yield. Such natural promoters are part of the DNA molecule according to the invention.

The invention furthermore relates to a vector which comprises a DNA molecule according to the invention for use in a process for eliminating or altering natural acarbose biosynthesis genes in an acarbose-producing microorganism. Such a vector is preferably selected from the group consisting of pGM160 and vectors as described in European Patents EP 0 334 282 and EP 0 158 872.

The invention furthermore relates to a host cell which is transformed with one of the above-described DNA molecules or vectors, in particular characterized in that said host cell is selected from the group consisting of *E. coli, Bacillus subtilis, Actinomycetales*, such as *Streptomyces, Actinoplanes, Ampullariella* or *Streptosporangium* strains, *Streptomyces hygroscopicus* var. *limoneus* or *Streptomyces glaucescens*, and also biotechnologically relevant fungi (e.g. *Aspergillus niger* and *Penicillium chrysogenum*) and yeasts (e.g. *Saccharomyces cerevisiae*); it is very particularly preferred for it to be selected from the group consisting of *Streptomyces glaucescens* GLA.O and *Actinoplanes* sp.

The invention furthermore relates to a protein mixture which can be obtained by expressing the genes of the recombinant DNA molecule according to the invention, comprising genes for biosynthesizing acarbose and homologous pseudo-oligosaccharides, in particular characterized in that the DNA molecule (a) comprises a DNA sequence according to Table 4, or parts thereof;

(b) comprises a DNA sequence which is able to hybridize, under stringent conditions, with the DNA molecule according to (a) or parts thereof; or (c) comprises a DNA sequence which, because of the degeneracy of the genetic code, differs from the DNA molecules according to (a) and (b) but which permits the expression of the proteins which can correspondingly be expressed using the DNA molecule according to (a) and (b), or parts thereof.

The invention furthermore relates to isolated proteins which can be obtained by expressing the genes which are encoded by the DNA molecule described in the previous paragraph.

The following statements apply to all the individual genes identified within the context of the present invention and have only been brought together for reasons of clarity: the invention furthermore relates to a protein which is encoded by a recombinant DNA molecule as described in the last paragraph but one, in particular characterized in that it comprises the DNA sequence of nucleotides 1 to 720 or 720 to 2006 or 2268 to 3332 or 3332 to 4306 or 4380 to 5414 or 5676 to 6854 according to Table 4 or parts thereof; a protein is very particularly preferred which is encoded by the acbA gene or the acbB gene or the acbC gene or the acbD gene or the acbE gene or the acbF gene, and which comprises the amino acid sequence according to Table 4 or parts thereof.

The invention furthermore relates to a process for obtaining the proteins which were described above as being part of the subject-matter of the invention, which process is characterized in that (a) the proteins are expressed in a suitable host cell, in particular which is characterized in that said host cell is selected from the group consisting of *E. coli, Bacillus subtilis, Actinomycetales,* such as *Streptomyces, Actinoplanes, Ampullariella* or *Streptosporangium* strains, *Streptomyces, hygroscopicus* var. *limoneus* or *Streptomyces glaucescens*, and also biotechnologically relevant fungi (e.g. *Aspergillus niger* and *Penicillium chrysogenum*) and yeasts (e.g. *Saccharomyces cerevisiae*); with the host cell very particularly preferably being selected from the group consisting of *Streptomyces glaucescens* GLA.O and *Actinoplanes* sp., and (b) are isolated.

The invention furthermore relates to a process for preparing acarbose, characterized in that (a) one or more genes of the recombinant DNA molecule which comprises a DNA sequence according to Table 4 or parts thereof or which comprises a DNA sequence which is able to hybridize, under stringent conditions, with the DNA molecule according to Table 4, or parts thereof, or which comprises a DNA sequence which, because of the degeneracy of the genetic code, differs from the DNA molecules which have just been described but which permits the expression of the proteins which can be correspondingly expressed using these DNA molecules, or parts thereof, is/are used for expression in a suitable host cell which is selected, in particular, from the same group as in the last paragraph, and (b) the acarbose is isolated from culture supernatants of said host cell.

The invention furthermore relates to a process for preparing acarbose, characterized in that (a) one or more genes of the recombinant DNA molecule which comprises a DNA sequence according to Table 4 or parts thereof or which comprises a DNA sequence which is able to hybridize, under stringent conditions, with the DNA molecule according to Table 4, or parts thereof, or which comprises a DNA sequence which, because of the degeneracy of the genetic code, differs from the DNA molecules which have just been described but which permits expression of the proteins which can be correspondingly expressed using the DNA molecules, or parts thereof, are eliminated in an acarbose-producing host cell, in particular *Streptomyces glaucescens* GLA.O and *Actinoplanes* sp., and (b) the acarbose is isolated from said host cell.

In this connection, the elimination of one or more genes can be effected by means of standard molecular biological methods, for example using the above-described vectors (pGM160 and others). A gene to be eliminated could, for example, be the acbE gene, which propably has a regulatory function. Genes could likewise be eliminated with the aim of obtaining pure acarbose as the only fermentation product and no longer obtaining a mixture of homologous pseudo-oligosaccharides (see above). The elimination of said genes is preferably achieved using the vectors which have been described above for this purpose.

The invention furthermore relates to a process for preparing acarbose, characterized in that the processes for preparing acarbose which have been described in the previous two paragraphs are combined with each other, such that, therefore, one or more of said genes is/are expressed artificially and one or more of said genes is/are eliminated.

The invention furthermore relates to a process for altering the gene expression of endogenous acarbose biosynthesis genes by mutating the respective gene promoter in order to obtain improved yields of acarbose. In this context, known methods of homologous recombination can be used to introduce the mutations into the production strain to be improved. These mutations can be transitions, deletions and/or additions. An "addition" can, for example, denote the addition of one single nucleotide or several nucleotides or of one or more DNA sequences which have a positive regulatory effect and which bring about an enhancement of the expression of an endogenous gene for biosynthesizing acarbose. The converse case, i.e. the addition of a DNA sequence which has a negative regulatory effect for repressing an endogenous acarbose biosynthesis gene is also a preferred form of an addition. "Transitions" may, for example, be nucleotide exchanges which reduce or amplify the effect of regulatory elements which act negatively or positively. "Deletions" can be used to remove regulatory elements which act negatively or positively. The endogenous genes of this process are preferably present in *Actinomycetales,* such as *Streptomyces, Actinoplanes, Ampullariella* or *Streptosporangium* strains, *Streptomyces hygroscopicus* var. *limoneus* or *Streptomyces glaucescens*; very particularly, they are present in *Streptomyces glaucescens* GLA.O and *Actinoplanes* sp.

The invention furthermore relates to the use of *Streptomyces* GLA.O for obtaining acarbose.

The invention furthermore relates to the use of *Streptomyces* GLA.O for preparing mutants of this strain by the "classical route", which mutants make it possible to achieve a more abundant production of acarbose. The methods for preparing improved natural product producers of this nature have been known for a long time and frequently make use of classical steps of mutagenesis and selection.

The invention furthermore relates to a process for completing the gene cluster for biosynthesizing acarbose and homologous polysaccharides according to Table 4, characterized in that a) hybridization probes which are derived from the DNA molecule according to Table 4 are prepared, b) these hybridization probes are used for the genomic screening of DNA libraries obtained from *Streptomyces glaucescens* GLA.O, and c) the clones which are found are isolated and characterized.

The invention furthermore relates to a process for completing the gene cluster for biosynthesizing acarbose and homologous pseudo-oligosaccharides according to Table 4, characterized in that, proceeding from the recombinant DNA molecule according to Table 4, a) PCR primers are prepared, b) these PCR primers are used to accumulate DNA fragments of genomic DNA from *Streptomyces glaucescens* GLA.O, with these primers being combined with those primers which hybridize from sequences of the vector system employed, c) the accumulated fragments are isolated and characterized.

The invention furthermore relates to a process for isolating a gene cluster for biosynthesizing acarbose and homologous pseudo-oligosaccharides from acarbose-producing microorganisms other than *Streptomyces glaucescens* GLA.O, characterized in that, proceeding from the recombinant DNA molecule according to claim 4, a) hybridization probes are prepared, b) these hybridization probes are used for the genomic or cDNA screening of DNA libraries which have been obtained from the corresponding microorganism, and c) the clones which are found are isolated and characterized.

The invention furthermore relates to a process for isolating a gene cluster for biosynthesizing acarbose and homologous pseudo-oligosaccharides from acarbose-producing microorganisms other than *Streptomyces glaucescens* GLA.O, characterized in that, proceeding from the recombinant DNA molecule according to claim 4, a) PCR primers are prepared, b) these PCR primers are used for accumulating DNA fragments of gemonic DNA or cDNA from a corresponding microorganism, c) the accumulated fragments are isolated and characterized, and d) where appropriate, employed in a process as described in the previous paragraph.

The described processes for isolating a gene cluster for the biosynthesis of acarbose and homologous pseudo-oligosaccharides from acarbose-producing microorganisms other than *Streptomyces glaucescens* GLA.O are characterized in that the microorganisms are selected from the group consisting of *Actinomycetales*, such as *Streptomyces, Actinoplanes, Ampullariella* and *Streptosporangium* strains, *Streptomyces hygroscopicus* var. *limoneus* and *Streptomyces glaucescens*, preferably from the group consisting of *Streptomyces glaucescens* GLA.O and *Actinoplanes* sp.

The invention furthermore relates to the use of *Streptomyces glaucescens* GLA.O for isolating acarbose.

The invention will now be explained in more detail with the aid of the examples, tables and figures, without being restricted thereto.

All the plasmid isolations were carried out using a Macherey and Nagel (Düren, Germany) isolation kit (Nucleobond®) in accordance with the manufacturer's instructions. Molecular biological procedures were carried out in accordance with standard protocols (Sambrock et al. (1989) Molecular cloning: A Laboratory Manual, 2nd ed. Cold Spring Harbor Laboratory, USA) or in accordance with the instructions of the respective manufacturer. DNA and protein sequences were examined using Genetics Computer Group Software, Version 8 (progams: FastA, TFastA, BlastX, Motifs, GAP and CODONPREFERENCE) and the SwissProt (release 32), EMBL (release 46) and Prosite (release 12.2) databases. The molecular biological manipulation of *Streptomyces glaucescens* and *Actinoplanes* (DNA isolation and DNA transformations) were carried out as described in Hopwood et al.: Genetic Manipulation of *Streptomyces* : A Laboratory Manual. The John Innes Foundation, Norwich, UK, 1985 and Motamedi and Hutchinson: Cloning and heterologous expression of a gene cluster for the biosynthesis of tetracenomycin C, the anthracycline antitumor antibiotic of *Streptomyces glaucescens*. Proc. Natl. Acad. Sci. USA 84:4445–4449 (1987).

In general, hybridizations were performed using the "Non-radioactive DNA labeling kit" from Boehringer Mannheim (Cat. No. 1175033). The DNA was visualized using the "Luminescent Detection Kit" from Boehringer Mannheim (Cat. No. 1363514). In all the examples given in this patent application, hybridization was carried out under stringent conditions: 68° C., 16 h. 5×SSC, 0.1% N-laurylsarcosine, 0.02% SDS, 1% Blocking Reagent (Boehringer Mannheim). SSC denotes 0.15M NaCl/0.015M sodium citrate. The definition of "stringent conditions" which is given here applies to all aspects of the present invention which refer to "stringent conditions". In this connection, the manner of achieving this stringency, i.e. the cited hybridization conditions, is not intended to have a limiting effect since the skilled person can select other conditions as well in order to achieve the same stringent conditions, e.g. by means of using other hybridization solutions in combination with other temperatures.

EXAMPLE 1

Synthesis and Sequences of the PCR Primers and Amplification of the Fragments from *S. glaucescens* GLA.O The PCR was carried out under standard conditions using in each case 100 pmol of primer 1 and of primer 2 in 100 µl of reaction mixture

| | |
|---|---|
| PCR buffer[1] | 10 µl |
| PCR primers | in each case 2.5 µl |
| dNTPs | in each case 0.2 mM |
| BSA (10 mg/ml) | 1 µl |
| Template DNA | 1 µg (1 µl) |
| Taq polymerase[2] (5 units/ml) | 1.5 µl |
| H$_2$O | to make up to 100 µl |

[1]Promega
[2]Boehringer Mannheim

The samples are overlaid with 75 µl of mineral oil and the amplification is carried out using a Perkin Elmer TC1 DNA thermal cyler.

Parameters:

| Cycles | Temperature | Duration |
|---|---|---|
| 1 | 96° C. | 5 min |
| | 74° C. | 5 min |
| 30 | 95° C. | 1.5 min |
| | 74° C. | 1.5 min |
| 1 | 74° C. | 5 min |

Table 1 lists the sequences of the degenerate primers which should be used for amplifying dTDP-glucose dehydratases from different *streptomycetes*.

TABLE 1

Primer sequences for amplifying dTDP-glucose 4,6-dehydratases

Primer 1: CSGGSGSSGCSGGSTTCATSGG (SEQ ID NO.:1)

Primer 2: GGGWVCTGGYVSGGSCCGTAGTTG (SEQ ID NO.:2)

In this table, S = G or C, W = A or T, V = A or G, and Y = T or C.

EXAMPLE 2

DNA Sequences of the PCR Fragments Isolated From *Streptomyces glaucescens* GLA.O The sequencing was performed by the dideoxy chain termination method of Sanger et al. (PNAS USA, 74: 5463–5467 (1977)). The reactions were carried out using the Auto Read Sequenzing Kit® from Pharmacia Biotech (Freiburg, Germany) in accordance with the manufacturer's instructions. An ALF DNA Sequencer® from Pharmacia Biotech (Freiburg, Germany) was used for separation and detection.

The subsequent cloning of the PCR fragments (Sure Clone Kit®, Pharmacia Biotech, Frieburg) into the *E. coli* vector pUC 18, and the sequencing of the fragment, provided support for the supposition that the fragment encoded a dTDP-glucose 4,6-dehydratase. However, 2 different genes were isolated which both exhibit high degrees of homology with dTDP-glucose 4,6-dehydratase but are not identical. In that which follows, the PCR fragments are designated acbD and HstrE.

The sequences of the isolated PCR fragments are shown in Table 2A and 2B and the homology comparison of the deduced amino acid sequences of HstrE and acbD is shown in Table 2C. The two proteins exhibit an identity of only 65%.

TABLE 2A

DNA sequence of acbD* (primer-binding sites are underlined, (SEQ ID NO.: 3)

```
                Primer 1
  1 CCCGGGCGGG GCGGGGTTCA TCGGCTCCGC CTACGTCCGC CGGCTCCTGT
 51 CGCCCGGGGC CCCCGGCGGC GTCGCGGTGA CCGTCCTCGA CAAACTCACC
101 TACGCCGGCA GCCTCGCCCG CCTGCACGCG GTGCGTGACC ATCCCGGCCT
151 CACCTTCGTC CAGGGCGACG TGTGCGACAC CGCGCTCGTC GACACGCTGG
201 CCGCGCGGCA CGACGACATC GTGCACTTCG CGGCCGAGTC GCACGTCGAC
251 CGCTCCATCA CCGACAGCGG TGCCTTCACC CGCACCAACG TGCTGGGCAC
301 CCAGGTCCTG CTCGACGCCG CGCTCCGCCA CGGTGTGCGC ACCCTCGTGC
351 ACGTCTCCAC CGACGAGGTG TACGGCTCCC TCCCGCACGG GGCCGCCGCG
401 GAGAGCGACC CCCTGCTCCC GACCTCGCCG TACGCGGCGT CGAAGGCGGC
451 CTCGGACCTC ATGGCGCTCG CCCACCACCG CACCCACGGC CTGGACGTCC
501 GGGTGACCCG CTGTTCGAAC AACTACGGCC CGCACCAGTT CCCGGG
                                           Primer 2
```

TABLE 2B

DNA sequence of HstrE* (primer-binding sites are underlined, (SEQ ID NO.: 4)

```
                Primer 2
  1 CCCCGGGTGC TGGTAGGGGC CGTAGTTGTT GGAGCAGCGG GTGATGCGCA
 51 CGTCCAGGCC GTGGCTGACG TGCATGGCCA GCGCGAGCAG GTCGCCCGAC
101 GCCTTGGAGG TGGCATAGGG GCTGTTGGGG CGCAGCGGCT CGTCCTCCGT
151 CCACGACCCC GTCTCCAGCG AGCCGTAGAC CTCGTCGGTG GACACCTGCA
201 CGAAGGGGGC CACGCCGTGC CGCAGGGCCG CGTCGAGGAG TGTCTGCGTG
251 CCGCCGGCGT TGGTCCGCAC GAACGCGGCG GCATCGAGCA GCGAGCGGTC
```

TABLE 2B-continued

DNA sequence of HstrE* (primer-binding sites are underlined, (SEQ ID NO.: 4)

```
301 CACGTGCGAC TCGGCGGCGA GGTGCACGAC CTGGTCCTGG CCGGCCATGA
351 CCCGGTCGAC CAGGTCCGCG TCGCAGATGT CGCCGTGGAC GAAGCGCAGC
401 CGGGGGTGGT CGCGGACCGG GTCGAGGTTG GCGAGGTTGC CGGCGTAGCT
451 CAGGGCGTCG AGCACGGTGA CGACGGCGTC GGGCGGCCCG TCCGGACCGA
501 GGAGGGTGCG GACGTAGTGC GAGCCCATGA ACCCCGCCGC C
                                   Primer 1
```

TABLE 2C

Homology comparison of the deduced amino acid sequences of the PCR products HstrE* and acbD* (program: GAP)

| | | | |
|---|---|---|---|
| Quality: | 196.3 | Length: | 182 |
| Ratio: | 1.091 | Gaps: | 0 |
| Percent similarity: | 77.654 | Percent identity: | 65.363 |

PCRstrE.Pep x PCRabcD.Pep

```
  1 ..AAGFMGSHYVRTLLGPDGPPDAVVTVLDALSYAGNLANLDPVRDHPRL   48
      :|||:||  |||  ||:|::|.:...|||||  |.|||.||.|.:|||||  |
  1 PGGAGFIGSAYVRRLLSPGAPGGVAVTVLDKLTYAGSLARLHAVRDHPGL   50

49 RFVHGDICDADLVDRVMAGQDQVVHLAAESHVDRSLLDAAAFVRTNAGGT   98
     ||:||:||..||| : | :|::||:|||||||||: |.:||.|||. ||
 51 TFVQGDVCDTALVDTLAARHDDIVHFAAESHVDRSITDSGAFTRTNVLGT  100

99 QTLLDAALRHGVAPFVQVSTDEVYGSLETGSWTEDEPLRPNSPYATSKAS  148
     |.||||||||||  .:|:|||||||||||. |. .|.:|| |.||||.|||.
101 QVLLDAALRHGVRTLVHVSTDEVYGSLPHGAAAESDPLLPTSPYAASKAA  150

149 GDLLALAMHVSHGLDVRITRCSNNYGPYQHPG                   180
     :||:|||  |  .|||||:|||||||||.| |
151 SDLMALAHHRTHGLDVRVTRCSNNYGPHQFP.                   181
``` in each case, upper row: SEQ ID NO.:5
in each case, lower row: SEQ ID NO.:6

EXAMPLE 3

Southern Analysis Using Chromosomal DNA From Streptomyces glaucescens GLA.O and the Isolated and Labeled PCR Fragments The cells were grown in R2YENG medium and harvested for the DNA isolation after 30 h. The chromosomal DNA was isolated from S. glaucescens GLA.O as described in Hopwood et al. (1985) Genetic manipulations of Streptomyces: a laboratory manual. The John Innes Foundation, Norwich UK).

A Southern blot analysis was carried out using the S. glaucescens GLA.O producer strain chromosomal DNA, which was digested with PstI, BgIII and BamHI, using the labeled probes consisting of the acbD and HstrE PCR fragments. The two PCR fragments were labeled with digoxygenin in accordance with the manufacturer's (Boehringer Mannheim; Mannheim) instructions, and a digest of the Streptomyces glaucescens GLA.O producer strain chromosomal DNA was separated on an agarose gel. The DNA was transferred by capillary transfer to nylon membranes and DNA regions which were homologous with the labeled probes were subsequently visualized following hybridization.

The two genes label different DNA regions (FIG. 1 and FIG. 2), with the fragments which were labeled by HstrE having to be gene fragments from Streptomyces glaucescens GLA.O hydroxystreptomycin biosynthesis. While the DNA sequence is not published, the high degree of homology of the protein sequence deduced from HstrE with StrE (Pissowotzki et al. (1991) Mol. Gen. Genet. 231: 113–123) from Streptomyces griseus N2-3-11 streptomycin biosynthesis (82% identity) and the concordance of the HstrE-labeled DNA fragments (FIG. 1) with the published restriction map of the Streptomyces glaucescens GLA.O hydroxystreptomycin gene cluster (Retzlaff et al. (1993) Industrial Microorganisms. Basic and applied molecular genetics ASM, Washington D.C., USA) permits this conclusion. The fragments which were labeled by the acbD probe (FIG. 2) belong to a DNA region which has not previously been investigated. This region encodes the enzymes for biosynthesizing the Streptomyces glaucescens GLA.O pseudo-oligosaccharides.

EXAMPLE 4

Cloning the 6.8 kb PstI Fragment

Inter alia, the acbD PCR fragment labels a 6.8 kB PstI DNA fragment (FIG. 2). This DNA fragment was isolated as follows. The region of the gel was excised with a razor blade and the DNA was isolated from the gel using an isolation kit from Pharmacia Biotech and cloned into plasmid pUC19 which had been cut with the restriction enzyme PstI (plasmid pacb1); this latter plasmid was then transformed into the E. coli strain DH5α. The individual clones were subcultured from these plates and a plasmid DNA isolation was carried out using these clones. A PCR amplification using the above-described primers 1 and 2 (Tab. 1) was carried out using the DNA from these clones (250). In this manner, the appropriate E. coli clone containing the 6.8 kb PstI fragment was isolated.

EXAMPLE 5

Sequencing the Isolated 6.8 kb PstI DNA Fragment

The DNA was digested with various restriction enzymes and individual DNA fragments were cloned into pUC19. The DNA sequence of the entire fragment, which is shown in Tab. 4 (SEQ ID NO.: 7), was then determined. The DNA sequence of the 6.8 kb PstI fragment was only partially confirmed by supplementary sequencing of the opposing strand. Several open reading frames, encoding various proteins, were found (programs: CODONPREFERENCE and BlastX). A total of 6 coding regions was found, i.e. a gene having a high degree of homology with ATP-binding protein, acbA, an aminotransferase acbB, a dTDP-glucose synthase acbC, a dTDP-glucose dehydratase acbD, a regulatory gene having homologies with the LacI protein family acbE, and a protein having similarities to sugar-binding proteins acbF. The sequences of the acbA and acbF genes were only determined in part. The homologies with other proteins from the databases, and the properties of the putative proteins, are summarized in Tab. 3. FIG. 3 shows, in summary form, a restriction map of the fragment, containing the most important restriction cleavage sites mentioned in the text, and the arrangement of the identified open reading frames.

TABLE 3

Analysis of the identified open reading frames on the 6.8 kb PstI fragment from Streptomyces glaucescens GLA.O

| ORF | Amino acid | MW | FastA[$] | % Identity | Accession number[$] |
|---|---|---|---|---|---|
| acbA | 239 | * | MalK, E. coli | 29% | P02914 |
| acbB | 429 | 45618 | DgdA, Burkholderia cepacia | 32% | P16932 |
| acbC | 355 | 37552 | StrD, Streptomyces griseus | 60% | P08075 |
| acbD | 325 | 35341 | StrE, Streptomyces griseus | 62% | P29782 |
| acbE | 345 | 36549 | DegA, Bacillus subtilis | 31% | P37947 |
| acbF | 396 | * | MalE, E. coli | 22% | P02928 |

*incomplete open reading frame;
[$]Swiss-Prot database (release 32)

EXAMPLE 6

Deletion of Genes acbBCD for Pseudo-Oligosaccharide Biosynthesis from the Streptomyces glaucescens GLA.O Chromosome Evidence that the identified DNA fragment encoded pseudo-oligosaccharide biosynthesis genes was produced as follows. A 3.4 kb gene region (EcoR1/SstI fragment b, FIG. 3) was replaced with the erythromycin resistance gene (1.6 kb) and cloned, together with flanking DNA regions from the 6.8 kb PstI fragment (pacb1) into the temperature-sensitive plasmid pGM160. The plasmid was constructed as described in the following: the 2.2 kb EcoR1/HindIII fragment (c, FIG. 3) from plasmid pacb1 was cloned into pGEM7zf (Promega, Madison, Wis., USA; plasmid pacb2), and the 1 kb SstI fragment from pacb1 (a, FIG. 3) was cloned into pUC19 (plasmid pacb3). A ligation was then carried out using the following fragments. The plasmid pGM160 (Muth et al. (1989) Mol. Gen Genet. 219:341–348) was cut with BamH/HindIII, the plasmid pacb2 was cut with XbaI/BamHI (c, FIG. 3), the plasmid pacb3 was cut with EcoRI/HindIII (a, FIG. 3), and the plasmid pIJ4026 (Bibb et al. (1985) Gene 38:215–226) was cut with EcoRI/XbaI in order to isolate the 1.6 kb ermE resistance gene.

The fragments were ligated in a mixture and transformed into E. coli DH5α and selected on ampicillin. The resulting plasmid, i.e. pacb4, was isolated from E. coli DH5α, tested for its correctness by means of restriction digestion and then transferred by protoplast transformation into S. glaucescens GLA.O. The transformants were selected with thiostrepton at 27° C. in R2YENG agar. The transformants were subsequently incubated at the non-permissive temperature of 39° C. and integration of the plasmid into the genome by way of homologous recombination thereby instituted (selection with thiostrepton (25 µg/ml) and erythromycin (50 µg/ml)). Under these conditions, the only clones which can grow are those in which the plasmid has become integrated into the genome. The corresponding clones were isolated, caused to sporulate (medium 1, see below) and plated out on erythromycin-containing agar (medium 1). Individual clones were isolated once again from this plate and streaked out on both thiostrepton-containing medium and erythromycin-containing medium. The clones which were erythromycin-resistant but no longer thiostrepton-resistant were analyzed. In these clones, the acbBCD genes had been replaced with ermE. Several clones were examined and the strain S. glaucescens GLA.O Δacb was finally selected as the reference strain (erythromycin-resistant, thiostrepton-sensitive) for further investigation.

| Medium 1 | |
|---|---|
| Yeast extract | 4 g/L |
| Malt extract | 10 g/L |
| Glucose | 4 g/L |
| Agar | 15 g/L |
| pH | 7.2 |

A further experiment examined whether the corresponding strain still produced acarbose. Some clones were grown and investigated for formation of the α-amylase inhibitor in a bioassay; however, no activity was found. The mutants were subsequently further characterized by means of Southern hybridization. Integration of the ermE gene had taken place at the predicted site. FIG. 4 shows a Southern hybridization which was carried out with the wild type and with the Streptomyces glaucescens GLA.O Δacb deletion mutant. The SstI fragment from pacb3 was used as the probe. The chromosomal DNA was isolated from the wild type and mutant and digested with the enzymes PstI and PstI/HindIII. The fragment pattern obtained for the deletion mutant corresponds to the predicted recombination event. The wild type exhibits the unchanged 6.8 kb PstI fragment, whereas the mutant exhibits a fragment which has been truncated by 1.8 kb (compare lanes 1 and 3, FIG. 4). Integration of the ermE resistance gene additionally introduced an internal HindIII cleavage site into the PstI fragment (compare lanes 2 and 4, FIG. 4).

EXAMPLE 7

Inhibition of α-amylase by Acarbose

Using an enzymic test for detecting starch (TC-Starch, Boehringer-Mannheim, Cat. No. 297748), it was possible to demonstrate that the compound isolated from *Streptomyces glaucescens* GLA.O inhibits α-amylase. Test principle: starch is cleaved into D-glucose by amyloglucosidase. The glucose is then converted with hexokinase into glucose-6-phosphate and the latter is converted with glucose-6-phosphate dehydrogenase into D-gluconate-6-phosphate. This reaction produces NADPH, whose formation can be determined photometrically. Acarbose inhibits the α-amylase and thereby prevents the formation of D-glucose and ultimately the formation of NADPH as well.

EXAMPLE 8

Medium for Growing *S. glaucescens* GLA.O and Producing Acarbose

The fermentation was carried out, at 27° C. on an orbital shaker at 120 rpm, in 500 ml Erlenmeyer flasks which were fitted with side baffles and which contained 100 ml of medium 2. The fermentation was terminated after 2 or 3 days. The pseudo-oligosaccharides were detected in a plate diffusion test as described in Example 9. No α-amylase inhibitors were produced when medium 3 was used. This means that the production of the pseudo-oligosaccharides is inhibited by glucose. Other sugars, such as maltose and sucrose, or complex sugar sources (malt extract) can also come into consideration for producing pseudo-oligosaccharides using *S. glaucescens* GLA.O.

| Medium 2: | |
|---|---|
| Soybean flour | 20 g/L |
| Starch | 20 g/L |
| pH | 7.2 |
| Medium 3: | |
| Soybean flour | 20 g/L |
| Glucose | 20 g/L |
| pH | 7.2 |

EXAMPLE 9

Biotest Using *Mucor miehei*

A suspension of spores of the strain *Mucor miehei* was poured into agar (medium 5) ($10^5$ spores/ml), and 10 ml of this mixture were in each case poured into Petri dishes. Paper test disks (6 mm diameter) were loaded with 10 μl of acarbose [lacuna] (1 mg/ml) or with a sample from an *S. glaucescens* culture and laid on the test plates. The plates were then incubated at 37° C. Inhibition halos appeared on the starch-containing medium 5. A plate which was prepared with glucose (medium 4) instead of starch was used as a control. On this medium, no inhibition halo formed around the filter disks loaded with active compound.

| Media 4 and 5: | |
|---|---|
| $KH_2PO_4$ x 3 $H_2O$ | 0.5 g |
| $MgSO_4$ x 7 $H_2O$ | 0.2 g |
| NaCl | 0.1 g |
| Ammonium sulfate | 5 g |
| Yeast nitrogen base | 1.7 g |
| Glucose (4) or starch (5) | 5 g |
| Agar | 15 g |

EXAMPLE 10

Transformation of *S. glaucescens* GLA.O

Protoplasts of the *Streptomyces glaucescens* strain were isolated as described in Motamedi and Hutchinson ((1987) PNAS USA 84: 4445–4449), and the isolated plasmid DNA was transferred into the cells by means of PEG transformation as explained in Hopwood et al. ((1985) Genetic manipulations of Streptomyces: a laboratory manual. The John Innes Foundation, Norwich UK). The protoplasts were regenerated on R2YENG medium at 30° C. (Motamedi and Hutchinson (1987) PNAS USA 84: 4445–4449). After 18 h, the agar plates were overlaid with a thiostrepton-containing solution and incubated at 30° C. (final concentration of thiostrepton: 20 μg/ml).

EXAMPLE 11

Isolation of the Pseudo-Oligosaccharides from *Streptomyces glaucescens* GLA.O, HPLC Analysis and Mass Spectroscopy Isolation The culture broth was separated from the mycelium by filtration. The culture filtrate which has been obtained in this way is then loaded onto an XAD16 column, after which the column is washed with water and the active components are eluted with 30% methanol. The eluate was concentrated down to the aqueous phase and the latter was extracted with ethyl acetate in order to remove lipophilic impurities. The aqueous phase was then concentrated and the active components were further purified in 5% methanol using a biogel P2 column. The individual fractions are collected in a fraction collector. The individual fractions were analyzed by means of the *Mucor miehei* biotest. Active eluates were rechromatographed, for further purification, in 5% methanol on biogel P2. The material which was isolated in this way was investigated by HPLC and MS.

HPLC

Column: Nucleosil® 100 C-18

Eluent 0.1% phosphoric acid=A/acetonitrile=B

Gradient: from 0 to 100% B in 15 min

Detection: 215 nm

Flow 2 ml/min

Injection volume: 10–20 μl

Using HPLC, it was not possible to distinguish the pseudo-oligosaccharide preparation from *S. glaucescens* GLA.O from authentic acarbose. Both the retention time and the UV absorption spectrum of the two components were identical in this eluent system. The pseudo-oligosaccharide mixture was not fractionated under these conditions.

Mass spectroscopic analysis (MS)

The molecular weights and the fragmentation pattern of authentic acarbose and the pseudo-oligosaccharides isolated from *Streptomyces glaucescens* GLA.O were determined by means of electrospray MS. Analysis of the acarbose which is commercially obtainable from Bayer (Glucobay) gave a mass peak at 645.5 (acarbose). The purified samples from *S. glaucescens* GLA.O contain a mixture of different pseudo-oligosaccharides whose sugar side chains are of different lengths: 969 (acarbose+2 glucose units), 807 (acarbose+1 glucose unit), 645 (corresponds to authentic acarbose). When acarbose and the compound which is isolated from *S. glaucescens* GLA.O and which has a molecular weight of 645 are fragmented, the same molecular fragments are formed, i.e.: 145 (4-amino-4,6-deoxyglucose), 303 (Acarviosin) and 465 (303 together with one glucose unit).

*Actinoplanes* sp. SE50 also produces a mixture of acarbose molecules having sugar side chains of different length (Truscheit (1984) VIIIth International Symposium on Medicinal Chemistry, Proc. Vol 1. Swedish Academy of Pharmaceutical Sciences, Stockholm, Sweden). The length of the sugar side chains can be influenced by the choice of the fermentation parameters and of the substrate in the nutrient solution.

EXAMPLE 12

Southern Hybridization Using *Actinoplanes* sp. SE50/110 (ATCC31044)

The chromosomal DNA was isolated from the strain *Actinoplanes* sp. SE50/100 and digested with restriction enzymes (PstI and BamHI). A Southern hybridization was then carried out using a probe which encompasses the coding region of the dTDP-glucose 4,6-dehydratase acbD from *Streptomyces glaucescens* GLA.O (fragment d, FIG. 3). The probe hybridizes with distinct bands from *Actinoplanes* sp. SE50/110 (FIG. 5, lanes 1 and 2). This provides the possibility of isolating the corresponding fragments from *Actinoplanes* sp. SE50/100 and other strain lines. Whether these DNA regions are in fact involved in the biosynthesis of acarbose remains to be demonstrated in subsequent investigations. Alternatively, the PCR primers 1 and 2 (Tab. 1) could also be used for amplifying the dTDP-glucose 4,6-dehydratase from *Actinoplanes* sp.

Legends:

FIG. 1: Southern hybridization using *S. glaucescens* GLA.O. Lane 1: PstI, lane 2: BamHI, lane 3: BglII. The labeled PCR fragment HstrE was used as the probe. Labeling of DNA fragments which are involved in the biosynthesis of hydroxy-streptomycin.

FIG. 2: Southern hybridization using *S. glaucescens* GLA.O. Lane 1: PstI, lane 2: BamHI, lane 3: BglII. The labeled PCR fragment acbD was used as the probe. Labeling of DNA fragments which are involved in the biosynthesis of the pseudo-oligosaccharides.

FIG. 3: Restriction map of the 6.8 kb PstI fragment from *Streptomyces glaucescens* GLA.O. Open reading frames and the direction in which each is transcribed are indicated by arrows. The fragments a, b, c and d identify DNA regions which are explained in more detail in the text.

FIG. 4: Southern hybridization using *Streptomyces glaucescens* Δacb: lane 1: PstI, lane 2: PstI/HindIII, and *Streptomyces glaucescens* GLA.O lane 3: PstI, lane 4: PstI/HindIII. The labeled 1.0 kb SstI fragment a (FIG. 3) was used as the probe.

FIG. 5: Southern hybridization using *Actinoplanes* sp. SE50/100: lane 1: PstI, lane 2: BamHI and *Streptomyces glaucescens* GLA.O lane 3: PstI. The labeled 1.0 kb SmaI/EcoRI fragment d (dTDP-glucose 4,6-hydratase, FIG. 3) was used as the probe. The arrows indicate the labeled DNA fragments (BamHI: 2.1 and 0.7 kb, PstI: ~11–12 kb)

Tab. 4: DNA sequence of the 6.8 kb PstI fragment from *Streptomyces glaucescens* GLA.O (SEQ ID NO.: 7). The deduced amino acid sequences (SEQ ID NO.: 8–13) of the identified open reading frames are given under the DNA sequences. Start and stop codons and potential ribosome binding sites are underlined.

acbA: SEQ ID NO.: 8
acbB: SEQ ID NO.: 9
acbC: SEQ ID NO.: 10
acbD: SEQ ID NO.: 11
acbE: SEQ ID NO.: 12
acbF: SEQ ID NO.: 13

TABLE 4

(SEQ ID NO.: 7, 8, 9, 10, 11, 12, 13)

```
P
s
t
I
CTGCAGGGTTCCCTGGTGCACGACCCGCCCCTGGTCGACGACCAGGGCGCTGTCGCAGAT
---------+---------+---------+---------+---------+---------+   60
GACGTCCCAAGGGACCACGTGCTGGGCGGGGACCAGCTGCTGGTCCCGCGACAGCGTCTA
  Q  L  T  G  Q  H  V  V  R  G  Q  D  V  V  L  A  S  D  C  I  -

CGCGGCGATGTCGGCGATGTCGTGGCTGGTGAGCACCACGGTGGTGCCCAGTTCCCGGTG
---------+---------+---------+---------+---------+---------+  120
GCGCCGCTACAGCCGCTACAGCACCGACCACTCGTGGTGCCACCACGGGTCAAGGGCCAC
  A  A  I  D  A  I  D  H  S  T  L  V  V  T  T  G  L  E  R  H  -

GGCGCGGTTGACCAGCCGGCGCACCGCGTCCTTCAGCACCATGTCGAGGCCGATCGTGGG
---------+---------+---------+---------+---------+---------+  180
CCGCGCCAACTGGTCGGCCGCGTGGCGCAGGAAGTCGTGGTACAGCTCCGGCTAGCACCC
  A  R  N  V  L  R  R  V  A  D  K  L  V  M  D  L  G  I  T  P  -

CTCGTCCCAGAACAGCACGGCCGGGTCGTGCAGCAGGCTCGCCGCGATCTCGGCGCGCAT
---------+---------+---------+---------+---------+---------+  240
GAGCAGGGTCTTGTCGTGCCGGCCCAGCACGTCGTCCGAGCGGCGCTAGAGCCGCGCGTA
  E  D  W  F  L  V  A  P  D  H  L  L  S  A  A  I  E  A  R  M  -
```

TABLE 4-continued (SEQ ID NO.: 7, 8, 9, 10, 11, 12, 13)

```
  S
  p
  h
  I
GCGCTGTCCGAGGCTGAGCTGCCGCACGGGGGTGGACCCCAGCGCGTCGATGTCGAGGAG
---------+---------+---------+---------+---------+---------+   300
CGCGACAGGCTCCGACTCGACGGCGTGCCCCCACCTGGGGTCGCGCAGCTACAGCTCCTC
   R  Q  G  L  S  L  Q  R  V  P  T  S  G  L  A  D  I  D  L  L  -

GTCCCGGAACAGGGCGAGGTTGCGCCGGTAGACCGGTCCGGGGATGTCGTAGATGCGGCG
---------+---------+---------+---------+---------+---------+   360
CAGGGCCTTGTCCCGCTCCAACGCGGCCATCTGGCCAGGCCCCTACAGCATCTACGCCGC
   D  R  F  L  A  L  N  R  R  Y  V  P  G  P  I  D  Y  I  R  R  -

K
                          p
                          n
                          I
CAGGATGCGGAAGGAGTCGGGTACCGACAGGTCCCACCAGAGCTGGCTGCGCTGGCCGAA
---------+---------+---------+---------+---------+---------+   420
GTCCTACGCCTTCCTCAGCCCATGGCTGTCCAGGGTGGTCTCGACCGACGCGACCGGCTT
     L  I  R  F  S  D  P  V  S  L  D  W  W  L  Q  S  R  Q  G  F  -

GACGACGCCGATCGTGCGGGCGTTGCGCTGCCGGTGCCGGTAGGGCTCCAGCCCGGCGAC
---------+---------+---------+---------+---------+---------+   480
CTGCTGCGGCTAGCACGCCCGCAACGCGACGGCCACGGCCATCCCGAGGTCGGGCCGCTG
   V  V  G  I  T  R  A  N  R  Q  R  H  R  Y  P  E  L  G  A  V  -

CGTGCAGCGGCCGGAGGTGGGGGTCATGATGCCGGTCAGCATCTTGATCGTGGTCGACTT
---------+---------+---------+---------+---------+---------+   540
GCACGTCGCCGGCCTCCACCCCCAGTACTACGGCCAGTCGTAGAACTAGCACCAGCTGAA
   T  C  R  G  S  T  P  T  M  I  G  T  L  M  K  I  T  T  S  K  -

GCCGGCTCCGTTGGCGCCGATGTAGGCGGTCTTCGTGCCGGCCGGTATCTCGAAGGAGAC
---------+---------+---------+---------+---------+---------+   600
CGGCCGAGGCAACCGCGGCTACATCCGCCAGAAGCACGGCCGGCCATAGAGCTTCCTCTG
   G  A  G  N  A  G  I  Y  A  T  K  T  G  A  P  I  E  F  S  V  -

K
                          p
                          n
                          I
GTCGTCGACGGCGCGCACGACGCGGTACCGGCGGGTCAGGAGGGTGGAGAGGCTGCCGAG
---------+---------+---------+---------+---------+---------+   660
CAGCAGCTGCCGCGCGTGCTGCGCCATGGCCGCCCAGTCCTCCCACCTCTCCGACGGCTC
   D  D  V  A  R  V  V  R  Y  R  R  T  L  L  T  S  L  S  G  L  -

CAGGCCGGGCTCGCGTTCGGCCAGCCGGAACTCCTTGACGAGGTGTTCGGCCACGATCAC
---------+---------+---------+---------+---------+---------+   720
GTCCGGCCCGAGCGCAAGCCGGTCGGCCTTGAGGAACTGCTCCACAAGCCGGTGCTAGTG
                                                        *
   L  G  P  E  R  E  A  L  R  F  E  K  V  L  H  E  A  V  I  V  -
                                                        ─────── acbA GCGATCACCCGCTCGACGGCCGTCTCCAGCAGGCGCAGGCCCTCGTCGAGCAGCGCCTCG
---------+---------+---------+---------+---------+---------+   780
CGCTAGTGGGCGAGCTGCCGGCAGAGGTCGTCCGCGTCCGGGAGCAGCTCGTCGCGGAGC
   A  I  V  R  E  V  A  T  E  L  L  R  L  G  E  D  L  L  A  E  -

TCGAGGGTGAACGGCGGTGCCAGCCGCAGGATGTGGCCGCCCAGGGAGGTGCGCAGCCCC
---------+---------+---------+---------+---------+---------+   840
AGCTCCCACTTGCCGCCACGGTCGGCGTCCTACACCGGCGGGTCCCTCCACGCGTCGGGG
   D  L  T  F  P  P  A  L  R  L  I  H  G  G  L  S  T  R  L  G  -

S
                          m
                          a
                          I
AGGTCGAGGGCGGTGGTGTAGACGGCCCCGGCGGTCTCGGGGGCGGGTGCCCGGCCGACG
---------+---------+---------+---------+---------+---------+   900
TCCAGCTCCCGCCACCACATCTGCCGGGGCCGCCAGAGCCCCCGCCCACGGGCCGGCTGC
   L  D  L  A  T  T  Y  V  A  R  A  T  E  P  A  P  A  R  G  V  -

GCGTCGGTGACGAACTCCAGGCCCACAGCAGTCCGAGGCCGCGTACCTGGCCGAGCTGG
---------+---------+---------+---------+---------+---------+   960
CGCAGCCACTGCTTGAGGTCCGGGGTGTCGTCAGGCTCCGGCGCATGGACCGGCTCGACC
   A  D  T  V  F  E  L  G  W  L  L  G  L  G  R  V  Q  G  L  Q  -
```

TABLE 4-continued (SEQ ID NO.: 7, 8, 9, 10, 11, 12, 13)

```
                                                S
                                                s
                                                t
                                                I
GGGAAGCGGGACTCCAGGGCGCGCAGCCGCTCCTGGATGAGCTCGCCGAGGACGCGCACG
---------+---------+---------+---------+---------+---------+  1020
CCCTTCGCCCTGAGGTCCCGCGCGTCGGCGAGGACCTACTCGAGCGGCTCCTGCGCGTGC
 P  F  R  S  E  L  A  R  L  R  E  Q  I  L  E  G  L  V  R  V   -

CGGTCGATCAGCCGGTCGCGCTCGACGACCTCCAGCGTGGCGCGGGCGGCGGCGATCCCC
---------+---------+---------+---------+---------+---------+  1080
GCCAGCTAGTCGGCCAGCGCGAGCTGCTGGAGGTCGCACCGCGCCCGCCGCCGCTAGGGG
 R  D  I  L  R  D  R  E  V  V  E  L  T  A  R  A  A  A  I  G   -

S
                                 m
                                 a
                                 I
AGTGGGTTGCTCGCGTACGTCGAGGCGTACGCCCCGGGGTGGCCGCCTCCGGCCTGCGCA
---------+---------+---------+---------+---------+---------+  1140
TCACCCAACGAGCGCATGCAGCTCCGCATGCGGGGCCCCACCGGCGGAGGCCGGACGCGT
 L  P  N  S  A  Y  T  S  A  Y  A  G  P  H  G  G  G  A  Q  A   -

GCTTCCGCGCGTCCGGCCAGCACGGCGAAGGGGAATCCGCTCGCGGTGCCCTTGGACAGC
---------+---------+---------+---------+---------+---------+  1200
CGAAGGCGCGCAGGCCGGTCGTGCCGCTTCCCCTTAGGCGAGCGCCACGGGAACCTGTCG
 A  E  A  R  G  A  L  V  A  F  P  F  G  S  A  T  G  K  S  L   -

ATCGCCAGGTCCGGCTCGATGCCGAACAGTTCGCTGGCGAGGAAGGCGCCGGTGCGCCCG
---------+---------+---------+---------+---------+---------+  1260
TAGCGGTCCAGGCCGAGCTACGGCTTGTCAAGCGACCGCTCCTTCCGCGGCCACGCGGGC
 M  A  L  D  P  E  I  G  F  L  E  S  A  L  F  A  G  T  R  G   -

CCGCCGGTGAGGACCTCGTCGGCGACGAGCAGCACGCCGCCGTCCCGGCAGGCGCCGGCG
---------+---------+---------+---------+---------+---------+  1320
GGCGGCCACTCCTGGAGCAGCCGCTGCTCGTCGTGCGGCGGCAGGGCCGTCCGCGGCCGC
 G  G  T  L  V  E  D  A  V  L  L  V  G  G  D  R  C  A  G  A   -

ATCCGCTCCCAGTAGCCGGGGGGCGGCACGATGACGCCTGCCGCGCCGAGGACGGGTTCG
---------+---------+---------+---------+---------+---------+  1380
TAGGCGAGGGTCATCGGCCCCCGCCGTGCTACTGCGGACGGCGCGGCTCCTGCCCAAGC
 I  R  E  W  Y  G  P  P  P  V  I  V  G  A  A  G  L  V  P  E   -

AAGACCAGGGCCGAGACGTTGGGCTTCTCCGCGATGTGCCGGCGCACGAGGGTCGCGCAC
---------+---------+---------+---------+---------+---------+  1440
TTCTGGTCCCGGCTCTGCAACCCGAAGAGGCGCTACACGGCCGCGTGCTCCCAGCGCGTG
 F  V  L  A  S  V  N  P  K  E  A  I  H  R  R  V  L  T  A  C   -

CGCACGTCGCACGAGGGGTACTCCAGGCCCAGGGGACAGCGGTAGCCAGTAGGGGCTGTA
---------+---------+---------+---------+---------+---------+  1500
GCGTGCAGCGTGCTCCCCATGAGGTCCGGGTCCCTGTCGCCATCGGTCATCCCCGACAT
 R  V  D  C  S  P  Y  E  L  G  L  P  C  R  Y  G  T  P  A  T   -

GCCAGCACGCTGTTGCCGCTGAAGGCCTGGTGGCCGATGTCCCAGTGGACCAGCATCCGG
---------+---------+---------+---------+---------+---------+  1560
CGGTCGTGCGACAACGGCGACTTCCGGACCACCGGCTACAGGGTCACCTGGTCGTAGGCC
 A  L  V  S  N  G  S  F  A  Q  H  G  I  D  W  H  V  L  M  R   -

GCGCCCATGGTCTTGCCGTGGAAGCCGTGGCGCAGGGCGCAGATCCGGTTGCGGCCCGGC
---------+---------+---------+---------+---------+---------+  1620
CGCGGGTACCAGAACGGCACCTTCGGCACCGCGTCCCGCGTCTAGGCCAACGCCGGGCCG
 A  G  M  T  K  G  H  F  G  H  R  L  A  C  I  R  N  R  G  P   -

GCGGCGGTCGCCTGGACGACCCGCAGGGCGGCCTCGACCACCTCCGCGCCGGTGGAGAAG
---------+---------+---------+---------+---------+---------+  1680
CGCCGCCAGCGGACCTGCTGGGCGTCCCGCCGGAGCTGGTGGAGGCGCGGCCACCTCTTC
 A  A  T  A  Q  V  V  R  L  A  A  E  V  V  E  A  G  T  S  F   -

AAGGCGTAGGTGTCGAGCTGTTCGGGCAGCAGCCTGGCGAGCAGTTCCAGCAGGCCGGCG
---------+---------+---------+---------+---------+---------+  1740
TTCCGCATCCACAGCTCGACAAGCCCGTCGTCGGACCGCTCGTCAAGGTCGTCCGGCCGC
 F  A  Y  T  D  L  Q  E  P  L  L  R  A  L  L  E  L  L  G  A   -

CGGTCCGGCGTGGCGCTGTCGTGGACGTTCCACAGGCGGCGGGCCTGGGTGGTGAGTGCC
---------+---------+---------+---------+---------+---------+  1800
GCCAGGCCGCACCGCGACAGCACCTGCAAGGTGTCCGCCGCCCGGACCCACCACTCACGG
```

TABLE 4-continued (SEQ ID NO.: 7, 8, 9, 10, 11, 12, 13)

```
       R  D  P  T  A  S  D  H  V  N  W  L  R  R  A  Q  T  T  L  A   -
     TCGACGACCTCCGGGTGCCCGTGGCCCAGTGACTGGGTGAGGGTCCCGGCCGCGAAGTCG
     ---------+---------+---------+---------+---------+---------+      1860
     AGCTGCTGGAGGCCCACGGGCACCGGGTCACTGACCCACTCCCAGGGCCGGCGCTTCAGC
       E  V  V  E  P  H  G  H  G  L  S  Q  T  L  T  G  A  A  F  D   -

AGGTACTGGTTGCCGTCCAGGTCGGTCAGAACGGGACCGCGTCCCTCGGCGAAGACCCGG
     ---------+---------+---------+---------+---------+---------+      1920
     TCCATGACCAACGGCAGGTCCAGCCAGTCTTGCCCTGGCGCAGGGAGCCGCTTCTGGGCC
       L  Y  Q  N  G  D  L  D  T  L  V  P  G  R  G  E  A  F  V  R   -

CGTCCGTGGACGGCTTCCTCGGAGGCGCCCGGCGCCAGGTGGCGGGCCTCCCGTGCCAGG
     ---------+---------+---------+---------+---------+---------+      1980
     GCAGGCACCTGCCGAAGGAGCCTCCGCGGGCCGCGGTCCACCGCCCGGAGGGCACGGTCC
       R  G  H  V  A  E  E  S  A  G  P  A  L  H  R  A  E  R  A  L   -

TGCTGTGTCTGCCGTAAGCCTGTCATCGCTGCCTCTGCTCGTCGGACCGGCTGACGCGAT
     ---------+---------+---------+---------+---------+---------+      2040
     ACGACACAGACGGCATTCGGACAGTAGCGACGGAGACGAGCAGCCTGGCCGACTGCGCTA
       H  Q  T  Q  R  L  G  T  M
                              ─────── acbB CGCCGGCGAACTGCGTTGTGGCGCACCACGGTTGGGGCGGCTCGGCGCTGAGTCAAACAC
     ---------+---------+---------+---------+---------+---------+      2100
     GCGGCCGCTTGACGCAACACCGCGTGGTGCCAACCCCGCCGAGCCGCGACTCAGTTTGTG TTGAACACACACCGCTGCAAGAGTTTGCGGGTTGTTTCAGAAAGTTGTTGCGAGCGGCCC
     ---------+---------+---------+---------+---------+---------+      2160
     AACTTGTGTGTGGCGACGTTCTCAAACGCCCAACAAAGTCTTTCAACAACGCTCGCCGGG CGGCACTCTGGTTGAGTCGACGTGCTTACGGCGCCACCACGCCTCACGTTCGAGGAGGGA
     ---------+---------+---------+---------+---------+---------+      2220
     GCCGTGAGACCAACTCAGCTGCACGAATGCCGCGGTGGTGCGGAGTGCAAGCTCCTCCCT CCTGTGAGAACAAGCCCGCAGACCGACCCGCTCCCGCGGAGGCCGAGGTGAAGGCCCTGG
     ---------+---------+---------+---------+---------+---------+      2280
     GGACACTCTTGTTCGGGCGTCTGGCTGGGCGAGGGCGCCTCCGGCTCCACTTCCGGGACC
                                                      V  K  A  L  V  -
                                                  acbC ──────

P
                                                                  v
                                                                  u
                                                                  I
                                                                  I
     TCCTGGCAGGTGGAACCGGCAGCAGACTGAGGCCGTTCACCCACACCGCCGCCAAGCAGC
     ---------+---------+---------+---------+---------+---------+      2340
     AGGACCGTCCACCTTGGCCGTCGTCTGACTCCGGCAAGTGGGTGTGGCGGCGGTTCGTCG
       L  A  G  G  T  G  S  R  L  R  P  F  T  H  T  A  A  K  Q  L   -

TGCTCCCCATCGCCAACAAGCCCGTGCTCTTCTACGCGCTGGAGTCCCTCGCCGCGGCGG
     ---------+---------+---------+---------+---------+---------+      2400
     ACGAGGGGTAGCGGTTGTTCGGGCACGAGAAGATGCGCGACCTCAGGGAGCGGCGCCGCC
       L  P  I  A  N  K  P  V  L  F  Y  A  L  E  S  L  A  A  A  G   -

GTGTCCGGGAGGCCGGCGTCGTCGTGGGCGCGTACGGCCGGGAGATCCGCGAACTCACCG
     ---------+---------+---------+---------+---------+---------+      2460
     CACAGGCCCTCCGGCCGCAGCAGCACCCGCGCATGCCGGCCCTCTAGGCGCTTGAGTGGC
       V  R  E  A  G  V  V  V  G  A  Y  G  R  E  I  R  E  L  T  G   -

GCGACGGCACCGCGTTCGGGTTACGCATCACCTACCTCCACCAGCCCCGCCCGCTCGGTC
     ---------+---------+---------+---------+---------+---------+      2520
     CGCTGCCGTGGCGCAAGCCCAATGCGTAGTGGATGGAGGTGGTCGGGCGGGCGAGCCAG
       D  G  T  A  F  G  L  R  I  T  Y  L  H  Q  P  R  P  L  G  L   -

TCGCGCACGCGGTGCGCATCGCCCGCGGCTTCCTGGGCGACGACGACTTCCTGCTGTACC
     ---------+---------+---------+---------+---------+---------+      2580
     AGCGCGTGCGCCACGCGTAGCGGGCGCCGAAGGACCCGCTGCTGCTGAAGGACGACATGG
       A  H  A  V  R  I  A  R  G  F  L  G  D  D  D  F  L  L  Y  L   -

TGGGGGACAACTACCTGCCCCAGGGCGTCACCGACTTCGCCCGCCAATCGGCCGCCGATC
     ---------+---------+---------+---------+---------+---------+      2640
     ACCCCCTGTTGATGGACGGGGTCCCGCAGTGGCTGAAGCGGGCGGTTAGCCGGCGGCTAG
       G  D  N  Y  L  P  Q  G  V  T  D  F  A  R  Q  S  A  A  D  P   -

CCGCGGCGGCCCGGCTGCTGCTCACCCCGGTCGCGGACCCGTCCGCCTTCGGCGTCGCGG
```

TABLE 4-continued (SEQ ID NO.: 7, 8, 9, 10, 11, 12, 13)

```
            ---------+---------+---------+---------+---------+---------+   2700
GGCGCCGCCGGGCCGACGACGAGTGGGGCCAGCGCCTGGGCAGGCGGAAGCCGCAGCGCC
  A   A   A   R   L   L   L   T   P   V   A   D   P   S   A   F   G   V   A   E   -

AGGTCGACGCGGACGGGAACGTGCTGCGCTTGGAGGAGAAACCCGACGTCCCGCGCAGCT
            ---------+---------+---------+---------+---------+---------+   2760
TCCAGCTGCGCCTGCCCTTGCACGACGCGAACCTCCTCTTTGGGCTGCAGGGCGCGTCGA
  V   D   A   D   G   N   V   L   R   L   E   E   K   P   D   V   P   R   S   S   -

CGCTCGCGCTCATCGGCGTGTACGCCTTCAGCCCGGCCGTCCACGAGGCGGTACGGGCCA
            ---------+---------+---------+---------+---------+---------+   2820
GCGAGCGCGAGTAGCCGCACATGCGGAAGTCGGGCCGGCAGGTGCTCCGCCATGCCCGGT
  L   A   L   I   G   V   Y   A   F   S   P   A   V   H   E   A   V   R   A   I   -

TCACCCCCTCCGCCCGCGGCGAGCTGGAGATCACCCACGCCGTGCAGTGGATGATCGACC
            ---------+---------+---------+---------+---------+---------+   2880
AGTGGGGGAGGCGGGCGCCGCTCGACCTCTAGTGGGTGCGGCACGTCACCTACTAGCTGG
  T   P   S   A   R   G   E   L   E   I   T   H   A   V   Q   W   M   I   D   R   -

GGGGCCTGCGCGTACGGGCCGAGACCACCACCCGGCCCTGGCGCGACACCGGCAGCGCGG
            ---------+---------+---------+---------+---------+---------+   2940
CCCCGGACGCGCATGCCCGGCTCTGGTGGTGGGCCGGGACCGCGCTGTGGCCGTCGCGCC
  G   L   R   V   R   A   E   T   T   T   R   P   W   R   D   T   G   S   A   E   -

AGGACATGCTGGAGGTCAACCGTCACGTCCTGGACGGACTGGAGGGCCGCATCGAGGGGA
            ---------+---------+---------+---------+---------+---------+   3000
TCCTGTACGACCTCCAGTTGGCAGTGCAGGACCTGCCTGACCTCCCGGCGTAGCTCCCCT
  D   M   L   E   V   N   R   H   V   L   D   G   L   E   G   R   I   E   G   K   -

AGGTCGACGCGCACAGCACGCTGGTCGGCCGGGTCCGGGTGGCCGAAGGCGCGATCGTGC
            ---------+---------+---------+---------+---------+---------+   3060
TCCAGCTGCGCGTGTCGTGCGACCAGCCGGCCCAGGCCCACCGGCTTCCGCGCTAGCACG
  V   D   A   H   S   T   L   V   G   R   V   R   V   A   E   G   A   I   V   R   -

GGGGGTCACACGTGGTGGGCCCGGTGGTGATCGGCGCGGGTGCCGTCGTCAGCAACTCCA
            ---------+---------+---------+---------+---------+---------+   3120
CCCCCAGTGTGCACCACCCGGGCCACCACTAGCCGCGCCCACGGCAGCAGTCGTTGAGGT
  G   S   H   V   V   G   P   V   V   I   G   A   G   A   V   V   S   N   S   S   -

GTGTCGGCCCGTACACCTCCATCGGGGAGGACTGCCGGGTCGAGGACAGCGCCATCGAGT
            ---------+---------+---------+---------+---------+---------+   3180
CACAGCCGGGCATGTGGAGGTAGCCCCTCCTGACGGCCCAGCTCCTGTCGCGGTAGCTCA
  V   G   P   Y   T   S   I   G   E   D   C   R   V   E   D   S   A   I   E   Y   -

ACTCCGTCCTGCTGCGCGGCGCCCAGGTCGAGGGGGCGTCCCGCATCGAGGCGTCCCTCA
            ---------+---------+---------+---------+---------+---------+   3240
TGAGGCAGGACGACGCGCCGCGGGTCCAGCTCCCCCGCAGGGCGTAGCTCCGCAGGGAGT
  S   V   L   L   R   G   A   Q   V   E   G   A   S   R   I   E   A   S   L   I   -

TCGGCCGCGGCGCCGTCGTCGGCCCGGCCCCCCGTCTCCCGCAGGCTCACCGACTGGTGA
            ---------+---------+---------+---------+---------+---------+   3300
AGCCGGCGCCGCGGCAGCAGCCGGGCCGGGGGGCAGAGGGCGTCCGAGTGGCTGACCACT
  G   R   G   A   V   V   G   P   A   P   R   L   P   Q   A   H   R   L   V   I   -

TCGGCGACCACAGCAAGGTGTATCTCACCCCATGACCACGACCATCCTCGTCACCGGCGG
            ---------+---------+---------+---------+---------+---------+   3360
AGCCGCTGGTGTCGTTCCACATAGAGTGGGGTACTGGTGCTGGTAGGAGCAGTGGCCGCC
                                        M   T   T   T   I   L   V   T   G   G
  G   D   H   S   K   V   Y   L   T   P   *
                                    acbD ———— s
                                                  m
                                                  a
                                                  I
AGCGGGCTTCATTCGCTCCGCCTACGTCCGCCGGCTCCTGTCGCCCGGGGCCCCCGGCGG
            ---------+---------+---------+---------+---------+---------+   3420
TCGCCCGAAGTAAGCGAGGCGGATGCAGGCGGCCGAGGACAGCGGGCCCCGGGGCCGCC
  A   G   F   I   R   S   A   Y   V   R   R   L   L   S   P   G   A   P   G   G   -

CGTCGCGGTGACCGTCCTCGACAAACTCACCTACGCCGGCAGCCTCGCCCGCCTGCACGC
            ---------+---------+---------+---------+---------+---------+   3480
GCAGCGCCACTGGCAGGAGCTGTTTGAGTGGATGCGGCCGTCGGAGCGGGCGGACGTGCG
  V   A   V   T   V   L   D   K   L   T   Y   A   G   S   L   A   R   L   H   A   -

GGTGCGTGACCATCCCGGCCTCACCTTCGTCCAGGGCGACGTGTGCGACACCGCGCTCGT
            ---------+---------+---------+---------+---------+---------+   3540
```

TABLE 4-continued (SEQ ID NO.: 7, 8, 9, 10, 11, 12, 13)

```
CCACGCACTGGTAGGGCCGGAGTGGAAGCAGGTCCCGCTGCACACGCTGTGGCGCGAGCA
 V   R   D   H   P   G   L   T   F   V   Q   G   D   V   C   D   T   A   L   V   -

CGACACGCTGGCCGCGCGGCACGACGACATCGTGCACTTCGCGGCCGAGTCGCACGTCGA
---------+---------+---------+---------+---------+---------+   3600
GCTGTGCGACCGGCGCGCCGTGCTGCTGTAGCACGTGAAGCGCCGGCTCAGCGTGCAGCT
 D   T   L   A   A   R   H   D   D   I   V   H   F   A   A   E   S   H   V   D   -

CCGCTCCATCACCGACAGCGGTGCCTTCACCCGCACCAACGTGCTGGGCACCCAGGTCCT
---------+---------+---------+---------+---------+---------+   3660
GGCGAGGTAGTGGCTGTCGCCACGGAAGTGGGCGTGGTTGCACGACCCGTGGGTCCAGGA
 R   S   I   T   D   S   G   A   F   T   R   T   N   V   L   G   T   Q   V   L   -

GCTCGACGCCGCGCTCCGCCACGGTGTGCGCACCTTCGTGCACGTCTCCACCGACGAGGT
---------+---------+---------+---------+---------+---------+   3720
CGAGCTGCGGCGCGAGGCGGTGCCACACGCGTGGAAGCACGTGCAGAGGTGGCTGCTCCA
 L   D   A   A   L   R   H   G   V   R   T   F   V   H   V   S   T   D   E   V   -

GTACGGCTCCCTCCCGCACGGGGCCGCCGCGGAGAGCGACCCCCTGCTTCCGACCTCGCC
---------+---------+---------+---------+---------+---------+   3780
CATGCCGAGGGAGGGCGTGCCCCGGCGGCGCCTCTCGCTGGGGGACGAAGGCTGGAGCGG
 Y   G   S   L   P   H   G   A   A   A   E   S   D   P   L   L   P   T   S   P   -

GTACGCGGCGTCGAAGGCGGCCTCGGACCTCATGGCGCTCGCCCACCACCGCACCCACGG
---------+---------+---------+---------+---------+---------+   3840
CATGCGCCGCAGCTTCCGCCGGAGCCTGGAGTACCGCGAGCGGGTGGTGGCGTGGGTGCC
 Y   A   A   S   K   A   A   S   D   L   M   A   L   A   H   H   R   T   H   G   -

CCTGGACGTCCGGGTGACCCGCTGTTCGAACAACTTCGGCCCCCACCAGCATCCCGAGAA
---------+---------+---------+---------+---------+---------+   3900
GGACCTGCAGGCCCACTGGGCGACAAGCTTGTTGAAGCCGGGGTGGTCGTAGGGCTCTT
 L   D   V   R   V   T   R   C   S   N   N   F   G   P   H   Q   H   P   E   K   -

GCTCATACCGCGCTTCCTGACCAGCCTCCTGTCCGGCGGCACCGTTCCCCTCTACGGCGA
---------+---------+---------+---------+---------+---------+   3960
CGAGTATGGCGCGAAGGACTGGTCGGAGGACAGGCCGCCGTGGCAAGGGGAGATGCCGCT
 L   I   P   R   F   L   T   S   L   L   S   G   G   T   V   P   L   Y   G   D   -

CGGGCGGCACGTGCGCGACTGGCTGCACGTCGACGACCACGTCAGGGCCGTCGAACTCGT
---------+---------+---------+---------+---------+---------+   4020
GCCCGCCGTGCACGCGCTGACCGACGTGCAGCTGCTGGTGCAGTCCCGGCAGCTTGAGCA
 G   R   H   V   R   D   W   L   H   V   D   D   H   V   R   A   V   E   L   V   -
                                       B
                                       g
                                       l
                                       I
                                       I
CCGCGTGTCGGGCCGGCCGGGAGAGATCTACAACATCGGGGCGGCACCTCGCTGCCCAA
---------+---------+---------+---------+---------+---------+   4080
GGCGCACAGCCCGGCCGGCCCTCTCTAGATGTTGTAGCCCCCGCCGTGGAGCGACGGGTT
 R   V   S   G   R   P   G   E   I   Y   N   I   G   G   G   T   S   L   P   N   -
             S
             s
             t
             I
CCTGGAGCTCACGCACCGGTTGCTCGCACTGTGCGGCGCGGGCCCGGAGCGCATCGTCCA
---------+---------+---------+---------+---------+---------+   4140
GGACCTCGAGTGCGTGGCCAACGAGCGTGACACGCCGCGCCCGGGCCTCGCGTAGCAGGT
 L   E   L   T   H   R   L   L   A   L   C   G   A   G   P   E   R   I   V   H   -

CGTCGAGAACCGCAAGGGGCACGACCGGCGCTACGCGGTCGACCACAGCAAGATCACCGC
---------+---------+---------+---------+---------+---------+   4200
GCAGCTCTTGGCGTTCCCCGTGCTGGCCGCGATGCGCCAGCTGGTGTCGTTCTAGTGGCG
 V   E   N   R   K   G   H   D   R   R   Y   A   V   D   H   S   K   I   T   A   -
                                     N
                                     r
                                     u
                                     I
GGAACTCGGTTACCGGCCGCGCACCGACTTCGCGACCGCGCTGGCCGACACCGCGAAGTG
---------+---------+---------+---------+---------+---------+   4260
CCTTGAGCCAATGGCCGGCGCGTGGCTGAAGCGCTGGCGCGACCGGCTGTGGCGCTTCAC
 E   L   G   Y   R   P   R   T   D   F   A   T   A   L   A   D   T   A   K   W   -

GTACGAGCGGCACGAGGACTGGTGGCGTCCCCTGCTCGCCGCGACATGACGTCGGGCCGG
```

TABLE 4-continued (SEQ ID NO.: 7, 8, 9, 10, 11, 12, 13)

```
CATGCTCGCCGTGCTCCTGACCACCGCAGGGGACGAGCGGCGCTGTACTGCAGCCCGGCC    4320
 Y   E   R   H   E   D   W   W   R   P   L   L   A   A   T   *

ACCGCAACCACCGGCCCCGGCCGGCACACCGCCGCCCGCGGCCGGTGGCCGGCCGGTCAG    4380
TGGCGTTGGTGGCCGGGGCCGGCCGTGTGGCGGCGGGCGCCGGCCACCGGCCGGCCAGTC
                                                            *

CGTCCGTGAGCCGGGCGCCGGCCGCCCCGCGGGCCGGCGGCGGTGGACCCCCGGACCACC    4440
GCAGGCACTCGGCCCGCGGCCGGCGGGGCGCCCGGCCGCCGCCACCTGGGGGCCTGGTGG
 R   G   H   A   P   R   R   G   G   R   P   G   A   A   T   S   G   R   V   V   -

E
              c
              o
              R
              I
AGTTCCGGCATGAAGACGAATTCGGTGCGCGGCGGCGGCGTTCCGCTCATCTCCTCCAGC    4500
TCAAGGCCGTACTTCTGCTTAAGCCACGCGCCGCCGCCGCAAGGCGAGTAGAGGAGGTCG
 L   E   P   M   F   V   F   E   T   R   P   P   P   T   G   S   M   E   E   L   -

AGTGCGTCCACGGCGACCTGCCCCATCGCCTTGACGGGCTGTCTGATGGTGGTCAGGGGA    4560
TCACGCAGGTGCCGCTGGACGGGGTAGCGGAACTGCCCGACAGACTACCACCAGTCCCCT
 L   A   D   V   A   V   Q   G   M   A   K   V   P   Q   R   I   T   T   L   P   -

GGGTCGGTGAAGGCCATGAGCGGCGAGTCGTCGAAGCCGACCACCGAGATGTCACCGGGA    4620
CCCAGCCACTTCCGGTACTCGCCGCTCAGCAGCTTCGGCTGGTGGCTCTACAGTGGCCCT
 P   D   T   F   A   M   L   P   S   D   D   F   G   V   V   S   I   D   G   P   -

ACCGTGAGACCCCGCCGGCGCGCGGCCCGACACGGCGCCGAGGGCCATCATGTCGCTGGCG    4680
TGGCACTCTGGGGCGGCCGCGCGCCGGGCGTGCCGCGGCTCCCGGTAGTACAGCGACCGC
 V   T   L   G   R   R   R   A   A   R   V   A   G   L   A   M   M   D   S   A   -

CACATGACGGCGGTGCAGCCCAGGTCGATCAGCGCGGACGCGGCGGCCTGGCCCCCCTCC    4740
GTGTACTGCCGCCACGTCGGGTCCAGCTAGTCGCGCCTGCGCCGCCGGACCGGGGGGAGG
 C   M   V   A   T   C   G   L   D   I   L   A   S   A   A   A   Q   G   G   E   -

S
                      s
                      t
                      I
AGGGAGAACAGCGAGTGCTGCACGAGCTCCTCGGACTCCCGCGCCGACACTCCCAGGTGC    4800
TCCCTCTTGTCGCTCACGACGTGCTCGAGGAGCCTGAGGGCGCGGCTGTGAGGGTCCACG
 L   S   F   L   S   H   Q   V   L   E   E   S   E   R   A   S   V   G   L   H   -

TCCCGCACGCCGGCCCGGAACCCCTCGATCTTCCGCTGCACCGGCACGAAGCGGGCGGGC    4860
AGGGCGTGCGGCCGGGCCTTGGGGAGCTAGAAGGCGACGTGGCCGTGCTTCGCCCGCCCG
 E   R   V   G   A   R   F   G   E   I   K   R   Q   V   P   V   F   R   A   P   -

CCGACGGCGAGGCCGACGCGCTCGTGCCCCAGCTCCGCCAGGTGCGCCACGCCAGGCGC    4920
GGCTGCCGCTCCGGCTGCGCGAGCACGGGGTCGAGGCGGTCCACGCGGTGCCGGTCCGCG
 G   V   A   L   G   V   R   E   H   G   L   E   A   L   H   A   V   A   L   R   -

ATCGCGGCCCCGGTCGTCCGGGGAGACGAAGGGTGCCTCGATCCGGGGCGAGAACCCGTTC    4980
TAGCGCCGGGCCAGCAGGCCCCTCTGCTTCCCACGGAGCTAGGCCCCGCTCTTGGGCAAG
 M   A   A   R   D   D   P   S   V   F   P   A   E   I   R   P   S   F   G   N   -

ACGAGGACGAAGGGCACCTGCCGCTCGTGCAGCCGGCCGTACCGTCCGGTCTCGGCGGTG    5040
TGCTCCTGCTTCCCGTGGACGGCGAGCACGTCGGCCGGCATGGCAGGCCAGAGCCGCCAC
 V   L   V   F   P   V   Q   R   E   H   L   R   G   Y   R   G   T   E   A   T   -

GTGTCCGCGTGCAGTCCGGAGACGAAGATGATGCCGGACACCCCGCGGTCCACGAGCATC    5100
CACAGGCGCACGTCAGGCCTCTGCTTCTACTACGGCCTGTGGGGCGCCAGGTGCTCGTAG
 T   D   A   H   L   G   S   V   F   I   I   G   S   V   G   R   D   V   L   M   -
```

TABLE 4-continued (SEQ ID NO.: 7, 8, 9, 10, 11, 12, 13)

```
                                    S
                                    m
                                    a
                                    I
TCCGTGAGTTCGTCCTCGGTCGAGCCGCCCGGGGTCTGCGTGGCGAGCACGGGCGTGTAG
---------+---------+---------+---------+---------+---------+  5160
AGGCACTCAAGCAGGAGCCAGCTCGGCGGGCCCCAGACGCACCGCTCGTGCCCGCACATC
  E  T  L  E  D  E  T  S  G  G  P  T  Q  T  A  L  V  P  T  Y  -

CCCTGACGCGTGAGCGCCTGCCCCATCACCTGGGCCAGTGCGGGGAAGAAGGGGTTGTCC
---------+---------+---------+---------+---------+---------+  5220
GGGACTGCGCACTCGCGGACGGGGTAGTGGACCCGGTCACGCCCCTTCTTCCCCAACAGG
  G  Q  R  T  L  A  Q  G  M  V  Q  A  L  A  P  F  F  P  N  D  -

AGTTCGGGGGTGACCAGTCCGACCAGCTCGGCGCGGCGCTGTCGCGCCGGCTGCTCGTAG
---------+---------+---------+---------+---------+---------+  5280
TCAAGCCCCCACTGGTCAGGCTGGTCGAGCCGCGCCGCGACAGCGCGGCCGACGAGCATC
  L  E  P  T  V  L  G  V  L  E  A  R  R  Q  R  A  P  Q  E  Y  -

CCCAGCGCGTCCAGTGCGGTCAGCACCGAGTCGCGGGTGCCGGTGGCCACACCGCGCGCA
---------+---------+---------+---------+---------+---------+  5340
GGGTCGCGCAGGTCACGCCAGTCGTGGCTCAGCGCCCACGGCCACCGGTGTGGCGCGCGT
  G  L  A  D  L  A  T  L  V  S  D  R  T  G  T  A  V  G  R  A  -

S
                                           m
                                           a
                                           I
CCGTTCAGCACCCGGCTGACCGTGGCCTTGCTGACGCCCGCCCGGGCTGCGATGTCGGCG
---------+---------+---------+---------+---------+---------+  5400
GGCAAGTCGTGGGCCGACTGGCACCGGAACGACTGCGGGCGGGCCCGACGCTACAGCCGC
  G  N  L  V  R  S  V  T  A  K  S  V  G  A  R  A  A  I  D  A  -

AGCCGCATGGTCATGGCAACGCACTCTACCTGTCGGGGCGTCAGGGCGTGCCCACCGCGC
---------+---------+---------+---------+---------+---------+  5460
TCGGCGTACCAGTACCGTTGCGTGAGATGGACAGCCCCGCAGTCCCGCACGGGTGGCGCG
  L  R  M  T  M
  ────────── acbE GCGGAACCGGCGGACTGCGGGGCACGGCCCGTCCGCCGCCCACGGACCACGCGCCCGAAA
---------+---------+---------+---------+---------+---------+  5520
CGCCTTGGCCGCCTGACGCCCCGTGCCGGGCAGGCGGCGGGTGCCTGGTGCGCGGGCTTT CGATGGCTGAAAATGCTTGCAGCAAATTGCCGCAACGTCTTTCGGCGGCTTTTCGATCCT
---------+---------+---------+---------+---------+---------+  5580
GCTACCGACTTTTACGAACGTCGTTTAACGGCGTTGCAGAAAGCCGCCGAAAAGCTAGGA GTTACGTTCCTGGCAACCCCGGCGCCGCGCAGAAGCGGTTGGCGTGAGGCGTCCAGACCT
---------+---------+---------+---------+---------+---------+  5640
CAATGCAAGGACCGTTGGGGCCGCGGCGCGTCTTCGCCAACCGCACTCCGCAGGTCTGGA CCGCCCGATTCCGGGATCACTCAGGGGAGTTCACAATGCGGCGTGGCATTGCGGCCACCG
---------+---------+---------+---------+---------+---------+  5700
GGCGGGCTAAGGCCCTAGTGAGTCCCCTCAAGTGTTACGCCGCACCGTAACGCCGGTGGC
                                 M  R  R  G  I  A  A  T  A  -
                                 acbF ──────────

CGCTGTTCGCGGCTGTGGCCATGACGGCATCGGCGTGTGGCGGGGGCGACAACGGCGGAA
---------+---------+---------+---------+---------+---------+  5760
GCGACAAGCGCCGACACCGGTACTGCCGTAGCCGCACACCGCCCCGCTGTTGCCGCCTT
  L  F  A  A  V  A  M  T  A  S  A  C  G  G  G  D  N  G  G  S  -

K
     p
     n
     I
GCGGTACCGACGCGGGCGGCACGGAGCTGTCGGGGACCGTCACCTTCTGGGACACGTCCA
---------+---------+---------+---------+---------+---------+  5820
CGCCATGGCTGCGCCCGCCGTGCCTCGACAGCCCCTGGCAGTGGAAGACCCTGTGCAGGT
  G  T  D  A  G  G  T  E  L  S  G  T  V  T  F  W  D  T  S  N  -

ACGAAGCCGAGAAGGCGACGTACCAGGCCCTCGCGGAGGGCTTCGAGAAGGAGCACCCGA
---------+---------+---------+---------+---------+---------+  5880
TGCTTCGGCTCTTCCGCTGCATGGTCCGGGAGCGCCTCCCGAAGCTCTTCCTCGTGGGCT
  E  A  E  K  A  T  Y  Q  A  L  A  E  G  F  E  K  E  H  P  K  -
```

TABLE 4-continued (SEQ ID NO.: 7, 8, 9, 10, 11, 12, 13)

```
AGGTCGACGTCAAGTACGTCAACGTCCCGTTCGGCGAGGCGAACGCCAAGTTCAAGAACG
---------+---------+---------+---------+---------+---------+   5940
TCCAGCTGCAGTTCATGCAGTTGCAGGGCAAGCCGCTCCGCTTGCGGTTCAAGTTCTTGC
  V  D  V  K  Y  V  N  V  P  F  G  E  A  N  A  K  F  K  N  A  -

CCGCGGGCGGCAACTCCGGTGCCCCGGACGTGATGCGTACGGAGGTCGCCTGGGTCGCGG
---------+---------+---------+---------+---------+---------+   6000
GGCGCCCGCCGTTGAGGCCACGGGGCCTGCACTACGCATGCCTCCAGCGGACCCAGCGCC
  A  G  G  N  S  G  A  P  D  V  M  R  T  E  V  A  W  V  A  D  -

ACTTCGCCAGCATCGGCTACCTCGCCCCGCTCGACGGCACGCCCGCCCTCGACGACGGGT
---------+---------+---------+---------+---------+---------+   6060
TGAAGCGGTCGTAGCCGATGGAGCGGGGCGAGCTGCCGTGCGGGCGGGAGCTGCTCCCCA
  F  A  S  I  G  Y  L  A  P  L  D  G  T  P  A  L  D  D  G  S  -

CGGACCACCTTCCCCAGGGCGGCAGCACCAGGTACGAGGGGAAGACCTACGCGGTCCCGC
---------+---------+---------+---------+---------+---------+   6120
GCCTGGTGGAAGGGGTCCCGCCGTCGTGGTCCATGCTCCCCTTCTGGATGCGCCAGGGCG
  D  H  L  P  Q  G  G  S  T  R  Y  E  G  K  T  Y  A  V  P  Q  -

AGGTGATCGACACCCTGGCGCTCTTCTACAACAAGGAACTGCTGACGAAGGCCGGTGTCG
---------+---------+---------+---------+---------+---------+   6180
TCCACTAGCTGTGGGACCGCGAGAAGATGTTGTTCCTTGACGACTGCTTCCGGCCACAGC
  V  I  D  T  L  A  L  F  Y  N  K  E  L  L  T  K  A  G  V  E  -

AGGTGCCGGGCTCCCTCGCCGAGCTGAAGACGGCCGCCGCCGAGATCACCGAGAAGACCG
---------+---------+---------+---------+---------+---------+   6240
TCCACGGCCCGAGGGAGCGGCTCGACTTCTGCCGGCGGCGGCTCTAGTGGCTCTTCTGGC
  V  P  G  S  L  A  E  L  K  T  A  A  A  E  I  T  E  K  T  G  -

GCGCGAGCGGCCTCTACTGCGGGGCGACGACCCGTACTTGGTTCCTGCCCTACCTCTACG
---------+---------+---------+---------+---------+---------+   6300
CGCGCTCGCCGGAGATGACGCCCCGCTGCTGGGCATGAACCAAGGACGGGATGGAGATGC
  A  S  G  L  Y  C  G  A  T  T  R  T  W  F  L  P  Y  L  Y  G  -

GGGAGGGCGGCGACCTGGTCGACGAGAAGAACAAGACCGTCACGGTCGACGACGAAGCCG
---------+---------+---------+---------+---------+---------+   6360
CCCTCCCGCCGCTGGACCAGCTGCTCTTCTTGTTCTGGCAGTGCCAGCTGCTGCTTGGGC
  E  G  G  D  L  V  D  E  K  N  K  T  V  T  V  D  D  E  A  G  -

GTGTGCGCGCCTACCGCGTCATCAAGGACCTCGTGGACAGCAAGGCGGCCATCACCGACG
---------+---------+---------+---------+---------+---------+   6420
CACACGCGCGGATGGCGCAGTAGTTCCTGGAGCACCTGTCGTTCCGCCGGTAGTGGCTGC
  V  R  A  Y  R  V  I  K  D  L  V  D  S  K  A  A  I  T  D  A  -

CGTCCGACGGCTGGAACAACATGCAGAACGCCTTCAAGTCGGGCAAGGTCGCCATGATGG
---------+---------+---------+---------+---------+---------+   6480
GCAGGCTGCCGACCTTGTTGTACGTCTTGCGGAAGTTCAGCCCGTTCCAGCGGTACTACC
  S  D  G  W  N  N  M  Q  N  A  F  K  S  G  K  V  A  M  M  V  -

TCAACGGCCCCTGGGCCATCGAGGACGTCAAGGCGGGAGCCCGCTTCAAGGACGCCGGCA
---------+---------+---------+---------+---------+---------+   6540
AGTTGCCGGGGACCCGGTAGCTCCTGCAGTTCCGCCCTCGGGCGAAGTTCCTGCGGCCGT
  N  G  P  W  A  I  E  D  V  K  A  G  A  R  F  K  D  A  G  N  -

ACCTGGGGGTCGCCCCCGTCCCGGCCGGCAGTGCCGGACAGGGCTCTCCCCAGGGCGGGT
---------+---------+---------+---------+---------+---------+   6600
TGGACCCCAGCGGGGGCAGGGCCGGCCGTCACGGCCTGTCCCGAGAGGGGTCCCGCCCA
  L  G  V  A  P  V  P  A  G  S  A  G  Q  G  S  P  Q  G  G  W  -

GGAACCTCTCGGTGTACGCGGGCTCGAAGAACCTCGACGCCTCCTACGCCTTCGTGAAGT
---------+---------+---------+---------+---------+---------+   6660
CCTTGGAGAGCCACATGCGCCCGAGCTTCTTGGAGCTGCGGAGGATGCGGAAGCACTTCA
  N  L  S  V  Y  A  G  S  K  N  L  D  A  S  Y  A  F  V  K  Y  -
                                                       S
                                                       s
                                                       t
                                                       I
ACATGAGCTCCGCCAAGGTGCAGCAGCAGACCACCGAGAAGCTGAGCCTGCTGCCCACCC
---------+---------+---------+---------+---------+---------+   6720
TGTACTCGAGGCGGTTCCACGTCGTCGTCTGGTGGCTCTTCGACTCGGACGACGGGTGGG
  M  S  S  A  K  V  Q  Q  Q  T  T  E  K  L  S  L  L  P  T  R  -

GCACGTCCGTCTACGAGGTCCCGTCCGTCGCGGACAACGAGATGGTGAAGTTCTTCAAGC
---------+---------+---------+---------+---------+---------+   6780
CGTGCAGGCAGATGCTCCAGGGCAGGCAGCGCCTGTTGCTCTACCACTTCAAGAAGTTCG
```

TABLE 4-continued (SEQ ID NO.: 7, 8, 9, 10, 11, 12, 13)

```
     T   S   V   Y   E   V   P   S   V   A   D   N   E   M   V   K   F   F   K   P   -
CGGCCGTCGACAAGGCCGTCGAACGGCCGTGGATCGCCGAGGGCAATGCCCTCTTCGAGC
---------+---------+---------+---------+---------+---------+  6840
GCCGGCAGCTGTTCCGGCAGCTTGCCGGCACCTAGCGGCTCCCGTTACGGGAGAAGCTCG
     A   V   D   K   A   V   E   R   P   W   I   A   E   G   N   A   L   F   E   P   -

P
             s
             t
             I
CGATCCGGCTGCAG
---------+---- 6854
GCTAGGCCGACGTC
    I   R   L   Q   -
```

---

What is claimed is:

1. A process for preparing acarbose, comprising the steps of:
   (i) transforming a host cell with a recombinant DNA molecule which comprises acarbose-synthesizing genes, and
   (ii) culturing said host cell under conditions such that said DNA molecule is expressed, and said acarbose is synthesized, and
   (iii) isolating said acarbose from culture supernatants of said host cell, wherein said DNA molecule is selected from the group consisting of (a) the nucleotide sequence of SEQ ID NO:7; (b) a nucleotide sequence which is capable of hybridizing, under stringent conditions, with the sequence of SEQ ID NO:7, wherein said nucleic acid that hybridizes to SEQ ID NO:7 encodes polpeptides capable of biosynthesizing acarbose, and (c) a nucleotide sequence which, because of the degeneracy of the genetic code differs from the nucleotide sequence of SEQ ID NO:7.

2. A process for preparing acarbose according to claim 1, wherein said host cell is selected from the group consisting of *E. coli, Bacillus subtilis, Streptomyces, Actinoplanes, Ampullariella* or *Streptosporangum* strains, *Streptomyces hygroscopicus* var. *limoneus* or *Streptomyces glaucescens, Aspergillus niger, Penicillium chrysogenum* and *Saccharomyces cerevisiae*.

* * * * *

UNITED STATES PATENT AND TRADEMARK OFFICE
CERTIFICATE OF CORRECTION

PATENT NO. : 6,825,013 B2
DATED : November 30, 2004
INVENTOR(S) : Decker Heinrich It is certified that error appears in the above-identified patent and that said Letters Patent is hereby corrected as shown below:

<u>Title page,</u>
Item [74], *Attorney, Agent, or Firm*, "Karen I. Krapen" should be changed to -- Karen I. Krupen --.

Signed and Sealed this

Twenty-fourth Day of May, 2005

JON W. DUDAS
*Director of the United States Patent and Trademark Office*